United States Patent [19]
Kai et al.

[11] Patent Number: 5,847,159
[45] Date of Patent: Dec. 8, 1998

[54] 1-[ω-(3,4-DIHYDRO-2-NAPHTHALENYL) ALKYL]-CYCLIC AMINE DERIVATIVES, PROCESS FOR PREPARING THE SAME, AND PHARMACEUTICAL COMPOSITION CONTAINING THE SAME

[75] Inventors: Naoki Kai, Amagasaki; Aki Kanehira, Suita; Toshiya Morie, Matsubara; Katsuhiko Hino, Nara-ken; Katsuyoshi Kawashima, Kobe; Isao Shimizu, Akashi; Kazuhisa Akiyama, Takatsuki, all of Japan

[73] Assignee: Dainippon Pharmaceutical Co., Ltd., Osaka, Japan

[21] Appl. No.: 930,603

[22] PCT Filed: Apr. 12, 1996

[86] PCT No.: PCT/JP96/01009
    § 371 Date: Oct. 14, 1997
    § 102(e) Date: Oct. 14, 1997

[87] PCT Pub. No.: WO96/33169
    PCT Pub. Date: Oct. 24, 1996

[30]     Foreign Application Priority Data

Apr. 15, 1995  [JP]  Japan .................. 7-113618

[51] Int. Cl.$^6$ .................. A61K 31/40; C07D 207/08
[52] U.S. Cl. .................. 548/578; 514/408; 540/450; 540/607; 546/206; 548/526; 548/541; 548/578
[58] Field of Search .................. 548/578, 541; 514/408

[56]      References Cited

U.S. PATENT DOCUMENTS 4,022,791  5/1977  Welch, Jr. .

OTHER PUBLICATIONS

Katsumi Itoh, et al., "Synthesis and Biological Activities of 3–Aminomethyl–1,2–dihydronaphthalene Derivatives", *Chemical Pharmaceutical Bulletin*, vol. 31, pp. 2006–2015, 1983.

C.C. Chan, et al., "2–Substituted Tetralin Derivatives as Conformationally Restricted Butyrophenone Analogs", *Pharmazie*, vol. 42, pp. 369–371, 1987.

Willard M. Welch, et al., "Analgesic and Tranquilizing Activity of 5,8–Distributed 2–Aminomethyl–3,4–dihydronaphthalenes", *Journal of Medicinal Chemistry*, vol. 21, No. 3, pp. 257–263, 1978.

*Primary Examiner*—Robert W. Ramsuer
*Attorney, Agent, or Firm*—Foley & Lardner

[57]         ABSTRACT

1-[ω-(3,4-Dihydro-2-naphthalenyl)alkyl]cyclic amine derivative of the formula (I):

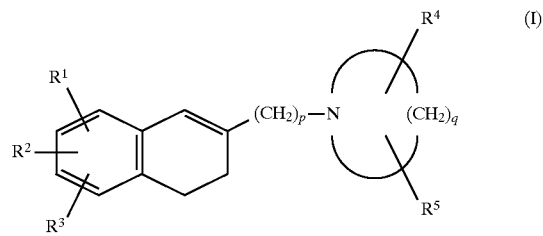

wherein $R^1$ and $R^2$ are H, halogen, OH, alkyl, alkoxy, hydroxymethyl, etc., or $R^1$ and $R^2$ combine to form methylenedioxy, trimethylene, etc., $R^3$ is H, etc., $R^4$ is H, OH, alkyl, etc., $R^5$ is H, alkyl, etc., p is integer of from 2 to 6, and q is integer of from 3 to 7, provided that when p is 2, and q is 5, $R^1$, $R^2$, $R^3$, $R^4$ and $R^5$ are not simultaneously H, or salts thereof, or N-oxide derivatives thereof, or a process for preparing the same, or pharmaceutical composition containing the same. The compounds of the present invention show potent inhibitory effect on the micturition reflex, and are useful as agents for treatment of frequent urination and urinary incontinence.

23 Claims, No Drawings

1-[ω-(3,4-DIHYDRO-2-NAPHTHALENYL) ALKYL]-CYCLIC AMINE DERIVATIVES, PROCESS FOR PREPARING THE SAME, AND PHARMACEUTICAL COMPOSITION CONTAINING THE SAME

This application is a 371 of PCT/JP96/01009 filed Apr. 12, 1996.

TECHNICAL FIELD

The present invention relates to a novel 1-[ω-(3,4-dihydro-2-naphthalenyl)alkyl]cyclic amine derivative showing an inhibitory effect on the micturition reflex, etc., process for preparing the same, and a pharmaceutical composition containing the same.

BACKGROUND ART

Hitherto, there are many reports on 1-[ω-(3,4-dihydro-2-naphthalenyl)-alkyl]cyclic amine derivatives.

However, as far as the present inventors know, the report on 1-[ω-(3,4-dihydro-2-naphthalenyl)alkyl]cyclic amine derivatives.

However, as far as the present inventors know, the report on 1-[ω-(3,4-dihydro-2-naphthalenyl)alkyl]cyclic amine derivative wherein the alkyl moiety is ethyl is only the following one. That is, Pharmazie, 42, 369 (1987) discloses that 1-[2-(3,4-dihydro-2-naphthalenyl)ethyl]piperidine hydrochloride shows a quite low affinity for dopamine receptor in vitro.

As a 1-[ω-(3,4-dihydro-2-naphthalenyl)alkyl]cyclic amine derivative wherein the alkyl moiety is methyl, the following compounds have been known.

U.S. Pat No. 4,022,791 discloses that the compound of the following formula is useful as analgesics and tranquilizing agents, and the paper of almost the same content is reported in J. Med. Chem., 21, 257 (1978).

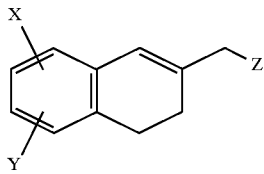

wherein X and Y are independently H, F, Cl, Br, an alkyl group having 1 to 4 carbon atoms, or an alkoxy group having 1 to 4 carbon atoms, and Z is a secondary or tertiary amino group, provided that X and Y are not simultaneously H.

Besides, Chem. Pharm. Bull., 31, 2006 (1983) discloses that the vasodilating and hypotensive activities of 1-[(3,4-dihydro-6-morpholino-2-naphthalenyl)methyl]piperazine and 4-benyzl-1-[(3,4-dihydro-6-morpholino-2-naphthalenyl)methyl]piperidine were tested by using dogs and spontaneously hypertensive rats.

With the advent of the increase in the aging people in the society, the number of patients suffering from frequent urination and urinary incontinence tends to increase year by year. At present, three medicines, i.e., flavoxate, oxybutynin and propiverine are clinically used in the treatment of these conditions, other than the medicaments for treatment of frequent urination and urinary incontinence accompanied by prostatic hypertrophy. All of these medicines exhibit their pharmacological activities (increase in bladder volume capacity) based on the relaxation of the bladder smooth muscle, and they are not necessarily satisfactory in terms of the less efficacy and difficulty for use in the case of frequent urination and urinary incontinence which is accompanied by urethral obstruction (difficulty in urination) as well as side effects.

Under the circumstances, the development of medicines for treatment of frequent urination and urinary incontinence via a central mechanism, which is different from those of existing medicines, has been tried. For example, 1-(4-ethylphenyl)-2-methyl-3-(1-pyrrolidinyl)-1-propanone hydrochloride (generic name: inaperisone hydrochloride), which is a central muscle relaxant (cf., Drugs Fut., 18, 375 (1993)), has been reported to be effective for the symptoms such as neurogenic bladder, unstable bladder, and nervous pollakisuria (cf., Nishinihon J. Urol., 54, 1472 and 1820 (1992)). However, the improvement of the efficacy and side effects thereof may not necessarily be sufficient.

The present inventors have intensively studied and have found that 1-[ω-(3,4-dihydro-2-naphthalenyl)alkyl]cyclic amine derivative of the following formula (I) exhibits a potent inhibitory effect mediated mainly via a central mechanism on the micturition reflex, and some of the compounds (I) show its potent inhibitory effect on the micturition reflex without the side effects such as depression on the central nerves and inhibition of spinal reflex.

DISCLOSURE OF INVENTION

The present invention provides a 1-[ω-(3,4-dihydro-2-naphthalenyl)-alkyl]cyclic amine derivative of the formula (I):

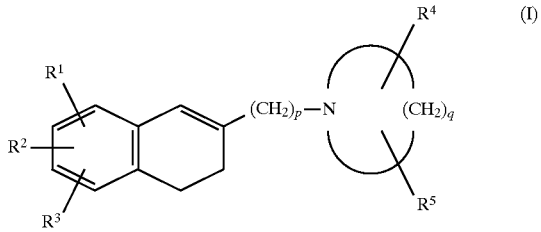

wherein $R^1$ and $R^2$ are the same or different and each a hydrogen atom, a halogen atom, a hydroxy group, a $C_1$–$C_5$ alkyl group, a $C_1$–$C_3$ alkoxy group, a hydroxymethyl group, a formyl group, a carboxyl group, or a $C_1$–$C_3$ alkoxycarbonyl group, or when $R^1$ and $R^2$ bond with carbon atoms being adjacent each other, then $R^1$ and $R^2$ may combine to form a methylenedioxy group, an ethylenoxy group (—$CH_2CH_2O$—), a trimethylene group, or a tetramethylene group; $R^3$ is a hydrogen atom, a halogen atom, a trifluoromethyl group, a $C_1$–$C_5$ alkyl group, a $C_1$–$C_3$ alkoxy group, or a phenyl group; $R^4$ is a hydrogen atom, a halogen atom, a hydroxy group, a $C_1$–$C_3$ alkyl group, or a ($C_1$–$C_2$ alkoxy) methyl group; $R^5$ is a hydrogen atom, a halogen atom, a $C_1$–$C_3$ alkyl group, or a ($C_1$–$C_2$ alkoxy)methyl group, or when $R^4$ and $R^5$ bond with a carbon atom other than the ones being next to the nitrogen atom, then $R^4$ and $R^5$ may combine to form an oxo group; p is an integer of from 2 to 6; and q is an integer of from 3 to 7, provided that when p is 2, and q is 5, then $R^1$, $R^2$, $R^3$, $R^4$ and $R^5$ are not simultaneously hydrogen atoms, a pharmaceutically acceptable acid addition salt thereof, and an N-oxide derivative thereof, a process for preparing the same, and a pharmaceutical composition containing the same.

The pharmaceutically acceptable acid addition salt of the compound of the formula (I) includes a salt with an inorganic acid such as hydrochloride, hydrobromide, hydroiodide, sulfate, or phosphate, or a salt with an organic acid such as oxalate, malonate, succinate, maleate, fumarate, lactate, malate, citrate, tartrate, benzoate, methanesulfonate, or p-toluenesulfonate. The compound of the formula (I), a salt thereof and an N-oxide derivative thereof may exist in the form of a hydrate or a solvate, and the present invention also includes these hydrates and solvates as well.

The compound of the formula (I) may have one or more asymmetric carbon atoms, and/or exhibit geometrical isomerism. Accordingly, the compound of the formula (I) may exist in the form of various stereoisomers. The present invention also includes these stereoisomers, a mixture thereof, and a racemic mixture thereof.

The terms used in the present description and claims are explained below.

The alkyl group and the alkyl moiety mean either straight chain or branched chain ones. The halogen atom includes fluorine, chlorine, bromine and iodine, and fluorine and chlorine are preferable, and the most preferable one is fluorine. Preferable groups for $R^1$ and $R^2$ are a hydrogen atom, a halogen atom (especially fluorine), a hydroxy group, a methyl group, an ethyl group, a propyl group, a methoxy group, an ethoxy group, a hydroxymethyl group, a carboxyl group, a methoxycarbonyl group, and an ethoxycarbonyl group. More preferable examples for $R^1$ and $R^2$ are a methyl group, an ethyl group, a methoxy group, an ethoxy group, and a hydroxymethyl group, and it is especially preferable for these groups to bond at 6-position and 7-position. Furthermore, it is more preferable that $R^1$ is a hydrogen atom or a halogen atom (especially fluorine), and $R^2$ is a halogen atom (especially fluorine), and among them, 6,7-dihalogen or 5-halogen is especially preferable.

Preferable group for $R^3$ is a hydrogen atom, and preferable groups for $R^4$ are a hydrogen atom, a halogen atom (especially fluorine), a hydroxy group, and a methyl group, and among them, a hydrogen atom and a methyl group are more preferable.

Preferable groups for $R^5$ are a hydrogen atom and a methyl group. In addition, it is preferable for $R^4$ and $R^5$ to combine to form an oxo group.

Preferred "p" is an integer of from 2 to 5, especially preferably 2, 3 or 4, and most preferably 2. Especially preferred "q" is 4 or 5, and most preferably 4.

Preferable compounds of the present invention are compounds of the formula (I) wherein $R^1$ and $R^2$ are the same or different and each a hydrogen atom, a halogen atom, a hydroxy group, a methyl group, an ethyl group, a propyl group, a methoxy group, an ethoxy group, a hydroxymethyl group, a carboxyl group, a methoxycarbonyl group, or an ethoxycarbonyl group, $R^3$ is a hydrogen atom, and $R^4$, $R^5$, p and q are the same as defined above, a pharmaceutically acceptable acid addition salt thereof, and an N-oxide derivative thereof.

More preferable compounds of the present invention are compounds of the formula (I) wherein $R^1$ and $R^2$ bond at 7-position and 6-position, respectively, and are the same or different, and each a methyl group, an ethyl group, a methoxy group, an ethoxy group, or a hydroxymethyl group, $R^3$ is a hydrogen atom, $R^4$ and $R^5$ are the same or different and each a hydrogen atom or a methyl group, p is an integer of from 2 to 5, and q is an integer of from 3 to 7, and a pharmaceutically acceptable acid addition salt thereof.

Other more preferable compounds are compounds of the formula (I) wherein $R^1$ is a hydrogen atom, $R^2$ is a 5-halogen atom, or $R^1$ and $R^2$ are each a halogen atom at 7-position and 6-position, respectively, and $R^3$ is a hydrogen atom, $R^4$ and $R^5$ are the same or different and each a hydrogen atom or a methyl group, p is an integer of from 2 to 5, and q is an integer of from 3 to 7, and a pharmaceutically acceptable acid addition salt thereof.

The most preferable compounds are compounds of the formula (I) wherein $R^1$ and $R^2$ bond at 7-position and 6-position, respectively, and are the same or different and each a methyl group, an ethyl group, a methoxy group, an ethoxy group, or a hydroxymethyl group, all of $R^3$, $R^4$ and $R^5$ are hydrogen atoms, p is 2, 3 or 4, and q is 4 or 5, and a pharmaceutically acceptable acid addition salt thereof.

Other most preferable compounds are compounds of the formula (I) wherein $R^1$ is a hydrogen atom, $R^2$ is 5-fluorine atom, or $R^1$ and $R^2$ are 7-fluorine atom and 6-fluorine atom, respectively, all of $R^3$, $R^4$ and $R^5$ are hydrogen atoms, p is 2, 3 or 4, and q is 4 or 5, and a pharmaceutically acceptable acid addition salt thereof.

The especially preferable compounds are compounds of the formula (Ia):

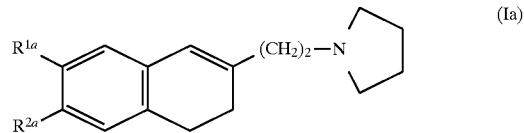

wherein $R^{1a}$ and $R^{2a}$ are the same or different, and each a methyl group, an ethyl group, a methoxy group, an ethoxy group, or a hydroxymethyl group, and a pharmaceutically acceptable acid addition salt thereof.

Suitable examples of the most preferable compounds of the present invention are the following compounds and a pharmaceutically acceptable acid addition salt thereof, and among them, the former four compounds are most preferable, and especially the former two compounds are most preferable.

1-[2-(3,4-dihydro-6,7-dimethyl-2-naphthalenyl)ethyl]pyrrolidine,

1-[2-(5-fluoro-3,4-dihydro-2-naphthalenyl)ethyl]pyrrolidine,

1-[2-(3,4-dihydro-6,7-dimethoxy-2-naphthalenyl)ethyl]pyrrolidine,

1-[2-(3,4-dihydro-7-methoxy-6-methyl-2-naphthalenyl)ethyl]pyrrolidine,

1-[2-(3,4-dihydro-6-hydroxymethyl-7-methyl-2-naphthalenyl)ethyl]-pyrrolidine,

1-[2-(6,7-diethyl-3,4-dihydro-2-naphthalenyl)ethyl]pyrrolidine,

1-[2-(6,7-difluoro-3,4-dihydro-2-naphthalenyl)ethyl]pyrrolidine, and

1-[2-(3,4-dihydro-6,7-dimethyl-2-naphthalenyl)ethyl]piperidine.

The representative compounds of the present invention are, in addition to the compounds of Examples described hereinafter, the compounds of the following Tables 1 and 2, and a pharmaceutically acceptable acid addition salt thereof, and an N-oxide derivative thereof. In the tables, Me means a methyl group, and Et means an ethyl group.

TABLE 1

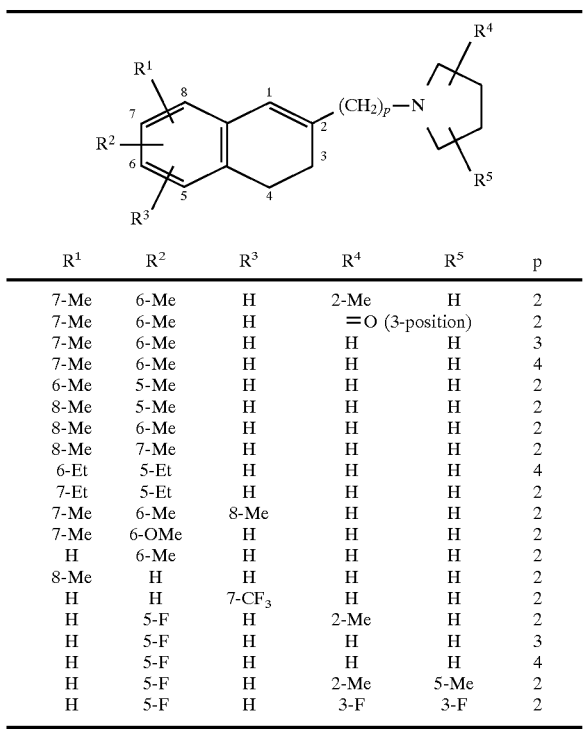

| R¹ | R² | R³ | R⁴ | R⁵ | p |
|---|---|---|---|---|---|
| 7-Me | 6-Me | H | 2-Me | H | 2 |
| 7-Me | 6-Me | H | =O (3-position) | | 2 |
| 7-Me | 6-Me | H | H | H | 3 |
| 7-Me | 6-Me | H | H | H | 4 |
| 6-Me | 5-Me | H | H | H | 2 |
| 8-Me | 5-Me | H | H | H | 2 |
| 8-Me | 6-Me | H | H | H | 2 |
| 8-Me | 7-Me | H | H | H | 2 |
| 6-Et | 5-Et | H | H | H | 4 |
| 7-Et | 5-Et | H | H | H | 2 |
| 7-Me | 6-Me | 8-Me | H | H | 2 |
| 7-Me | 6-OMe | H | H | H | 2 |
| H | 6-Me | H | H | H | 2 |
| 8-Me | H | H | H | H | 2 |
| H | H | 7-CF₃ | H | H | 2 |
| H | 5-F | H | 2-Me | H | 2 |
| H | 5-F | H | H | H | 3 |
| H | 5-F | H | H | H | 4 |
| H | 5-F | H | 2-Me | 5-Me | 2 |
| H | 5-F | H | 3-F | 3-F | 2 |

TABLE 2

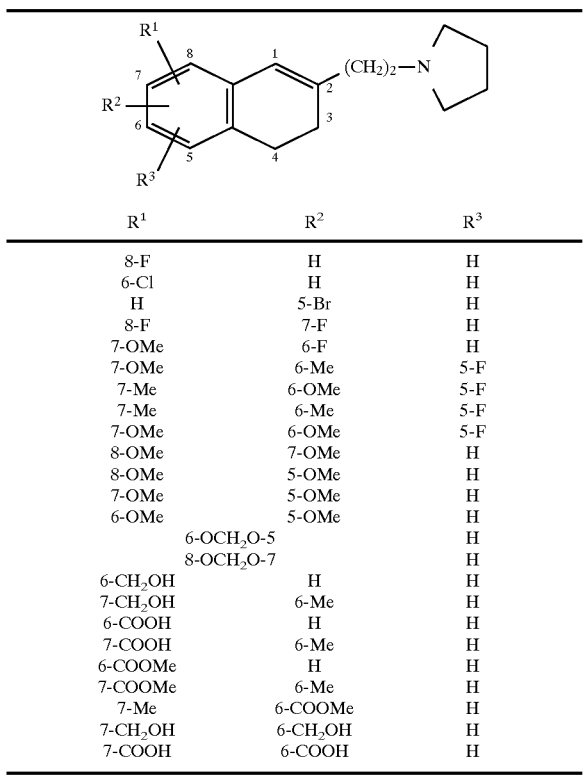

| R¹ | R² | R³ |
|---|---|---|
| 8-F | H | H |
| 6-Cl | H | H |
| H | 5-Br | H |
| 8-F | 7-F | H |
| 7-OMe | 6-F | H |
| 7-OMe | 6-Me | 5-F |
| 7-Me | 6-OMe | 5-F |
| 7-Me | 6-Me | 5-F |
| 7-OMe | 6-OMe | 5-F |
| 8-OMe | 7-OMe | H |
| 8-OMe | 5-OMe | H |
| 7-OMe | 5-OMe | H |
| 6-OMe | 5-OMe | H |
| 6-OCH₂O-5 | | H |
| 8-OCH₂O-7 | | H |
| 6-CH₂OH | H | H |
| 7-CH₂OH | 6-Me | H |
| 6-COOH | H | H |
| 7-COOH | 6-Me | H |
| 6-COOMe | H | H |
| 7-COOMe | 6-Me | H |
| 7-Me | 6-COOMe | H |
| 7-CH₂OH | 6-CH₂OH | H |
| 7-COOH | 6-COOH | H |

The compounds of the present invention may be prepared, for example, by the following processes.

Process (a):

The compound of the formula (I) is prepared by subjecting a compound of the formula (II):

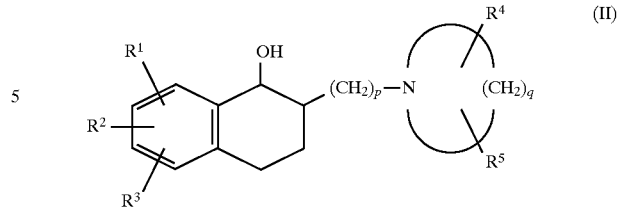

wherein $R^1$, $R^2$, $R^3$, $R^4$, $R^5$, p and q are the same as defined above, to dehydration.

The dehydration reaction is carried out under the conditions being suitable for the dehydration reaction of an alcohol into an olefine. For example, the compound of the formula (II) is reacted with a dehydrating agent in a suitable solvent or without a solvent. The dehydrating agent includes, for example, an inorganic acid (e.g., hydrogen chloride, hydrogen bromide, sulfuric acid, phosphoric acid, or boric acid), an organic acid (e.g., oxalic acid, formic acid, or trifluoroacetic acid), an aromatic sulfonic acid (e.g., p-toluenesulfonic acid), an organic acid anhydride (e.g., acetic anhydride), o-sulfobenzoic anhydride, an anhydrous inorganic salt (e.g., potassium hydrogen sulfate), an inorganic acid chloride (e.g., thionyl chloride or phosphorus oxychloride), an organic acid chloride (e.g., acetyl chloride), a sulfonic acid chloride (e.g., p-toluenesulfonyl chloride or methanesulfonyl chloride), a Lewis acid (e.g., boron fluoride-diethyl ether complex or zinc chloride), iodine, alumina, and silica gel. The solvent should be selected in accordance with, for example, the types of the dehydrating agent to be used, and includes, for example, aromatic hydrocarbons (e.g., benzene, toluene, and xylene), ethers (e.g., diethyl ether, tetrahydrofuran, or dioxane), ketones (e.g., acetone or ethyl methyl ketone), acetonitrile, alcohols (e.g., methanol, ethanol, or isopropyl alcohol), ethylene glycol, organic acids (e.g., formic acid, acetic acid, or propionic acid), pyridine, dimethylsulfoxide and water. These solvents may be used alone, or in a mixture of two or more solvents. The reaction temperature may vary depending, for example, on the types of the dehydration agent, but it is usually in the range of from about −20° C. to about 200° C. Besides, the compound of the formula (II) used in the dehydration reaction may be in the form of a complex with a boron-containing reducing agent such as boranes or a decomposed product thereof, which can be converted into the compound of the formula (I) with using an acidic dehydrating agent such as an inorganic acid or an organic acid.

The starting compound (II) may be prepared by the process of the following reaction scheme.

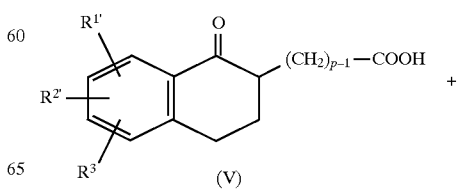

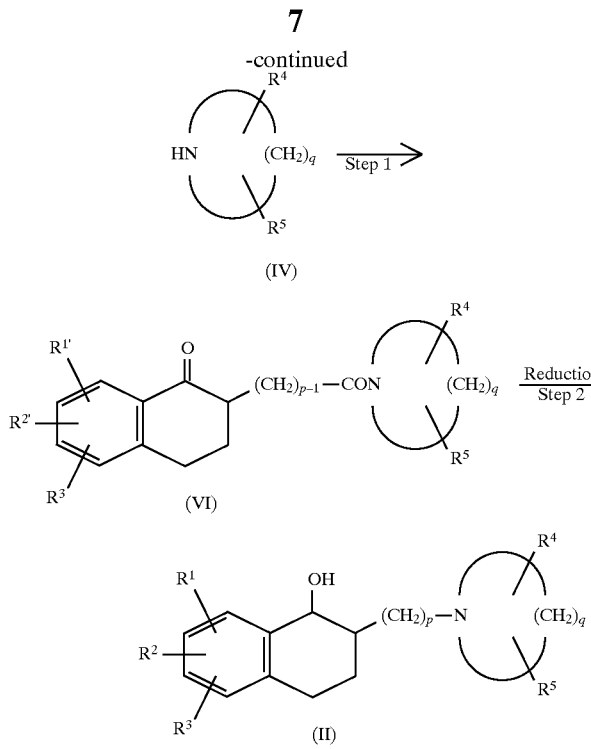

wherein $R^3$, $R^4$, $R^5$, p and q are the same as defined above, $R^{1'}$ and $R^{2'}$ are the same groups as those for $R^1$ and $R^2$ except that the formyl group and the carboxyl group are protected ones.

In the above reaction scheme, the protected formyl group for $R^{1'}$ and $R^{2'}$ includes, for example, acetals (e.g., dimethoxy methyl, diethoxy methyl, or ethylenedioxy methyl), oximes (e.g., hydroxyiminomethylene), and the protected carboxyl group includes, for example, a lower alkoxycarbonyl group (e.g., methoxycarbonyl or ethoxycarbonyl), an aralkyloxycarbonyl group (e.g., benzyloxycarbonyl).

Each step of the above reaction scheme is explained below.

Step 1

The present step is carried out by reacting the compound (V) or a reactive derivative thereof with the compound (IV) under the same conditions for the conventional amidation reactions.

The reactive derivative of the compound (V) includes, for example, a lower alkyl ester (especially, methyl ester), an activated ester, an acid anhydride, and an acid halide (especially, acid chloride). The activated ester includes, for example, p-nitrophenyl ester, 2,4,5-trichlorophenyl ester, and N-hydroxy-succinimide ester. The acid anhydride includes a symmetric acid anhydride and a mixed acid anhydride, and the mixed acid anhydride includes, for example, a mixed acid anhydride with an alkyl chlorocarbonate such as ethyl chlorocarbonate or isobutyl chlorocarbonate, a mixed acid anhydride with an aralkyl chlorocarbonate such as benzyl chlorocarbonate, and a mixed acid anhydride with an aryl chlorocarbonate such as phenyl chlorocarbonate, and a mixed acid anhydride with an alkanoic acid such as isovaleric acid or pivalic acid.

When the compound (V) per se is used in this step, the reaction is preferably carried out in the presence of a condensing agent such as N,N'-dicyclohexylcarbodiimide, 1-ethyl-3-(3-dimethylaminopropyl)carbodiimide hydrochloride, N,N'-carbonyldiimidazole, N,N'-carbonyldisuccinimide, 1-ethoxy-carbonyl-2-ethoxy-1,2-dihydroquinoline, diphenylphosphoryl azide, propane-phosphonic anhydride, or benzotriazol-1-yloxy tris (dimethylamino)-phosphonium hexafluorophosphate.

The reaction of the compound (V) or a reactive derivative thereof with the compound (IV) is carried out in a solvent or without a solvent. The solvent should be selected in accordance with, for example, the types of the starting compound to be used, and includes, for example, aromatic hydrocarbons (e.g., benzene, toluene, and xylene), ethers (e.g., diethyl ether, tetrahydrofuran, and dioxane), halogenated hydrocarbons (e.g., dichloromethane and chloroform), alcohols (e.g., ethanol and isopropyl alcohol), ethyl acetate, acetone, acetonitrile, dimethylformamide, 1,3-dimethyl-2-imidazolidinone, dimethyl sulfoxide, ethylene glycol, and water. These solvents may be used alone, or in a mixture of two or more solvents. The reaction is optionally carried out in the presence of a base, if necessary, and the base includes, for example, an alkali hydroxide (e.g., sodium hydroxide or potassium hydroxide), an alkali carbonate (e.g., sodium carbonate or potassium carbonate), an alkali hydrogen carbonate (e.g., sodium hydrogen carbonate or potassium hydrogen carbonate), or an organic base (e.g., triethyl amine, tributyl amine, diisopropylethyl amine, or N-methylmorpholine), but an excess amount of the compound (IV) can act as a base instead. The reaction temperature may vary depending, for example, on the types of the starting compounds to be used, but it is usually in the range of from about −30° C. to about 200° C., preferably in the range of from about −10° C. to about 150° C.

The starting compound (V) of this step may be prepared from 3,4-dihydro-1(2H)-naphthalenones by a process known per se, for example, by the method disclosed in J. Med. Chem., 17, 273 (1974); Japanese Patent First Publication (Kokai) No. 54-24861 (Chem. Abstr., 91, 56702b (1979)); Pharmazie, 41, 835 (1986); Yakugaku Zasshi, 110, 561 and 922 (1990); Heterocycles, 34, 1303 (1992); Tetrahedron, 48, 4027 (1992), or the process disclosed in Reference Examples 1 to 3, or by a modified process thereof.

On the other hand, the starting 3,4-dihydro-1(2H)-naphthalenones for preparing the compound (V) may be commercially available ones, or can be prepared by a process known per se, for example, by the method disclosed in J. Chem. Soc., 1961, 4425; J. Org. Chem., 26,1109 (1961); J. Heterocycl. Chem., 10, 31 (1973); U.S. Pat. No. 4,022,791; Chem. Pharm. Bull., 25, 632 (1977); ibid., 31, 2006 (1983); J. Med. Chem., 17, 273 (1974); ibid., 50, 4933 (1985); Japanese Patent First Publication (Kokai) No. 6-87746; Synth. Commun., 21, 981 (1991); or Tetrahedron Lett., 33, 5499 (1992), or by a modified method thereof.

The another starting compound (IV) of this step may be commercially available ones, or can be prepared by a process known per se, for example, by the method disclosed in Synlett, 1995, 55, or by a modified method thereof.

The compound of the formula (VI) wherein p is 2 is also prepared by the methods of paragraphs (1) to (3) of Reference Example 9 or 12 described hereinafter, or by a modified method thereof.

Step 2

The present step is carried out by treating the compound (VI) with a reducing agent being suitable for reducing a carbonyl group of ketone into an alcoholic hydroxy group, and reducing a carbonyl group of amide into a methylene group in a suitable solvent. The reducing agent includes, for example, a hydride or hydride complex of aluminum such as lithium aluminum hydride, diisobutyl aluminum hydride, sodium bis(2-methoxyethoxy)aluminum hydride, or aluminum hydride, sodium borohydride, or a combination of sodium borohydride with a Lewis acid such as anhydrous aluminum chloride, cobalt (II) chloride, or boron fluoride-diethyl ether complex, a hydrogen complex of boron such as sodium acetoxyborohydride or sodium trifluoroacetoxyborohydride, boranes such as diborane, and triethylsilane-zinc chloride. The solvent should be selected in accordance with, for example, the types of the reducing agent to be used, and includes, for example, ethers (e.g., diethyl ether, tetrahydrofuran, dimethoxyethane, dioxane, and diglyme), aromatic hydrocarbons (e.g., benzene and toluene), halogenated hydrocarbons (e.g., dichloromethane and chloroform), alcohols (e.g., methanol and ethanol), acetic acid, and pyridine. These solvent may be used alone, or in a mixture of two or more solvents. The reaction temperature may vary depending, for example, on the types of the reducing agent to be used, but it is usually in the range of from about −10° C. to about 130° C. The reduction reaction may be carried out under inert atmosphere, for example, under nitrogen gas or argon gas. When the compound (VI) wherein $R^4$ and $R^5$ combine to form an oxo group is used in this step, it is preferable to protect said group prior to the reaction with a conventional protecting group such as an acetal (e.g., dimethyl acetal, diethyl acetal, or ethylene acetal), or an oxime. When the compound (VI) wherein $R^{1'}$ and/or $R^{2'}$ are a protected formyl group and/or a protected carboxyl group is used, the protecting groups in the product are removed by a conventional method after the reduction to give the compound (II). The compound (II) obtained in this step can be used in the above-mentioned subsequent dehydration reaction without isolation or purification. When a boron-containing reducing agent such as boranes is used as a reducing agent, the compound (II) is obtained in the form of a complex with a boron-containing reducing agent or a decomposed product thereof, which can also be used in the above-mentioned dehydration reaction as it is.

Process (b):

The compound of the formula (I) is also prepared by reacting a compound of the formula (III):

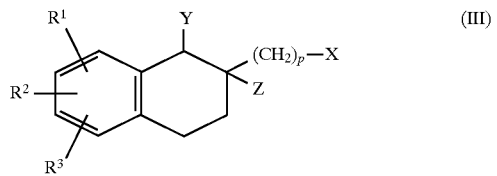

wherein $R^1$, $R^2$, $R^3$ and p are the same as defined above, X and Y are the same or different and each a reactive ester residue of an alcohol, and Z is a hydrogen atom, or Y and Z may combine to form a bond, with a compound of the formula (IV):

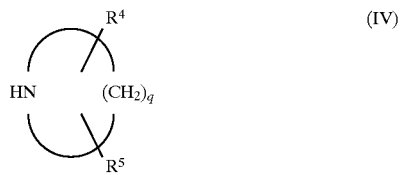

wherein $R^4$, $R^5$ and q are the same as defined above.

The reactive ester residue of an alcohol for X and Y of the formula (III) includes, for example, a halogen atom (e.g., chlorine, bromine, or iodine), a lower alkylsulfonyloxy group (e.g., methanesulfonyloxy or ethanesulfonyloxy), and an arylsulfonyloxy group (e.g., benzenesulfonyloxy, p-toluenesulfonyloxy, or m-nitrobenzenesulfonyloxy).

The reaction of the compound (III) and the compound (IV) is usually carried out in the presence of a base in a suitable solvent. The base includes, for example, an alkali carbonate (e.g., sodium carbonate or potassium carbonate), an organic base (e.g., triethylamine, tributylamine, diisopropylethylamine, or N-methylmorpholine), an alkali metal alkoxide (e.g., sodium methoxide or sodium ethoxide), and an alkali metal hydride (e.g., sodium hydride or potassium hydride), but an excess amount of the compound (IV) can act as a base instead. The solvent should be selected in accordance with, for example, the types of the starting compounds and the bases to be used, and includes, for example, aromatic hydrocarbons (e.g., benzene and toluene), ethers (e.g., tetrahydrofuran, dioxane, and diglyme), halogenated hydrocarbons (e.g., dichloromethane and chloroform), ketones (e.g., acetone and ethyl methyl ketone), acetonitrile, alcohols (e.g., methanol, ethanol, and isopropyl alcohol), dimethylformamide, and 1,3-dimethyl-2-imidazolidinone. These solvents may be used alone, or in a mixture of two or more thereof. The reaction temperature may vary depending, for example, on the types of the starting compounds to be used, and it is usually in the range of from about 30° C. to about 150° C., preferably in the range of from about 80° C. to about 120° C.

The starting compound (III) is prepared by a process known per se, for example, by the method of Reference Examples 10 and 11 described hereinafter, or by a modified method thereof.

When the compound (I) wherein $R^1$ and/or $R^2$ are a $C_1-C_3$ alkoxy-carbonyl group is obtained in the above Process (a) or (b), said compound (I) can be converted into the compound (I) wherein $R^1$ and/or $R^2$ are a formyl group or a hydroxymethyl group by reduction in a conventional manner, or into the compound (1) wherein $R^1$ and/or $R^2$ are a carboxyl group by hydrolysis in a conventional manner. The conversion into the hydroxymethyl group is illustrated in Example 71 described hereinafter. The conversion into the carboxyl group is illustrated in Example 73. The conversion into the formyl group is carried out by reduction at a temperature of from about −78° C. to about −50° C. with using a hydride or hydrogen complex of aluminum (e.g., lithium aluminum hydride, diisobutyl aluminum hydride, or sodium bis(2-methoxy-ethoxy)aluminum hydride) as a reducing agent.

The compound (I) obtained in the above Processes can be isolated and purified by a conventional method such as chromatography, recrystallization, or re-precipitation. The compound (I) is obtained either in the free base form or in the form of an acid addition salt thereof, according to the types of the starting compounds, the reaction conditions, etc. The acid addition salt is converted into a free base by a conventional method, for example, by treating it with a base (e.g., alkali carbonate or alkali hydroxide). On the other hand, the free base can be converted into an acid addition salt thereof by treating it with various acids by a conventional method.

Further, the compound (I) can be converted into an N-oxide derivative at the cyclic amine moiety thereof by oxidizing it under conventional N-oxidation conditions. The N-oxidation reaction is carried out by reacting the compound (I) with an oxidizing agent in a suitable solvent. The oxidizing agent includes, for example, hydrogen peroxide, and organic peracids such as peracetic acid, perbenzoic acid, m-chloroperbenzoic acid, and mono-perphthalic acid. The oxidizing agent is usually used in an amount of from about 0.9 to about 2 equivalents, to the amount of the compound (I). The solvent should be selected in accordance with, for example, the types of the oxidizing agent to be used, and includes, for example, water, acetic acid, alcohols (e.g., methanol and ethanol), ketones (e.g., acetone), ethers (e.g., diethyl ether and dioxane), and halogenated hydrocarbons (e.g., dichloromethane and chloroform). The reaction temperature may vary depending, for example, on the types of the oxidizing agent to be used, and it is usually in the range of from about −30° C. to about 100° C., preferably in the range of from about −20° C. to about 30° C.

The pharmacological activities of the compounds of the present invention are illustrated by the following pharmacological experiments on the representative compounds of the present invention, and inaperisone hydrochloride (hereinafter, optionally referred to as "Compound A"), which is a known centrally acting agent for treatment of frequent urination and urinary incontinence.

EXPERIMENT 1

Inhibitory effect on rhythmic bladder contractions (micturition reflex)

The experiment was carried out according to the method of Maggi, C. A. and Meli, A. [J. Pharmacol. Methods,10, 79 (1983)]. It is generally accepted that the rhythmic bladder contractions evoked by instillation of saline solution into the bladder are mediated via the micturition reflex pathway like that of natural urination.

Female Std-Wistar rats weighing 160–190 g were used in groups of 3–4 animals. Under urethane anesthesia (1 g/kg, s.c.), both ureters were tied and cut at the side of kidney after a mid line incision of the abdomen. A cannula, connected to a syringe and a pressure transducer, was inserted into the bladder via the external urethral orifice and ligated around the proximal urethra. The animal was allowed to stay for about 30 minutes after the operation. The bladder was slowly filled with warm saline solution (0.4–1 ml) by means of a syringe until rhythmic contractions were induced. The change of the intravesical pressure was recorded on a recorder via a pressure transducer. After the rhythmic contractions became constant, test compounds dissolved or suspended in 0.5% aqueous tragacanth solution were administered via the cannula inserted for intraduodenal administration. The effect of each compound on the contractile frequency was investigated every 15 minutes till two hours after the administration.

Table 3 shows the inhibitory effect on the contractile frequency (two hours) at the prescribed dose of each test compound or the dose of the test compound required for 50% inhibition of the contractile frequency ($ED_{50}$ value). The inhibitory rate on the contractile frequency (two hours) was expressed as the mean value of the inhibitory rates at an every 15-minute interval for two hours after the administration, which was determined based on the contractile frequency for 15 minutes before the administration. $ED_{50}$ value was determined by the method of Litchfield-Wilcoxon [J. Pharmacol. Exp. Ther., 96, 99 (1949)] on the basis of the inhibitory rates of the contractile frequency (two hours) at each dose.

TABLE 3

Inhibitory effect on rhythmic bladder contractions

| Test Comp. | Inhibitory effect on contractile frequency $ED_{50}$ (mg/kg, i.d.) or Dose; Inhibitory rate (%) | Test Comp. | Inhibitory effect on contractile frequency $ED_{50}$ (mg/kg, i.d.) or Dose; Inhibitory rate (%) |
|---|---|---|---|
| Ex. 1 | $ED_{50}$ = 4.3 mg/kg | Ex. 43 | $ED_{50}$ = 11.1 mg/kg |
| Ex. 2 | $ED_{50}$ = 4.4 mg/kg | Ex. 44 | 10 mg/kg; 34% |
| Ex. 3 | 10 mg/kg; 38% | Ex. 45 | 10 mg/kg; 48% |

TABLE 3-continued

Inhibitory effect on rhythmic bladder contractions

| Test Comp. | Inhibitory effect on contractile frequency $ED_{50}$ (mg/kg, i.d.) or Dose; Inhibitory rate (%) | Test Comp. | Inhibitory effect on contractile frequency $ED_{50}$ (mg/kg, i.d.) or Dose; Inhibitory rate (%) |
|---|---|---|---|
| Ex. 4 | $ED_{50}$ = 11.4 mg/kg | Ex. 46 | $ED_{50}$ = 12.4 mg/kg |
| Ex. 6 | 10 mg/kg; 42% | Ex. 47 | 10 mg/kg; 37% |
| Ex. 8 | 30 mg/kg; 62% | Ex. 49 | 10 mg/kg; 46% |
| Ex. 9 | 10 mg/kg; 47% | Ex. 50 | 10 mg/kg; 50% |
| Ex. 10 | 10 mg/kg; 33% | Ex. 52 | 10 mg/kg; 52% |
| Ex. 11 | 30 mg/kg; 60% | Ex. 53 | 10 mg/kg; 35% |
| Ex. 12 | 10 mg/kg; 35% | Ex. 54 | 10 mg/kg; 43% |
| Ex. 13 | 30 mg/kg; 77% | Ex. 55 | 10 mg/kg; 43% |
| Ex. 14 | 10 mg/kg; 49% | Ex. 56 | 10 mg/kg; 34% |
| Ex. 15 | 10 mg/kg; 44% | Ex. 58 | 10 mg/kg; 34% |
| Ex. 18 | 30 mg/kg; 51% | Ex. 60 | 10 mg/kg; 33% |
| Ex. 20 | 30 mg/kg; 67% | Ex. 62 | $ED_{50}$ = 6.1 mg/kg |
| Ex. 26 | $ED_{50}$ = 29.1 mg/kg | Ex. 66 | 10 mg/kg; 34% |
| Ex. 32 | 10 mg/kg; 47% | Ex. 68 | $ED_{50}$ = 7.4 mg/kg |
| Ex. 34 | 30 mg/kg; 65% | Ex. 72 | 10 mg/kg; 49% |
| Ex. 36 | $ED_{50}$ = 12.9 mg/kg | Ex. 74 | 10 mg/kg; 42% |
| Ex. 41 | 10 mg/kg; 38% | | |
| Comp.A | $ED_{50}$ = 34.8 mg/kg | | |

As is clear from Table 3, all the compounds of the present invention tested in this experiment exhibited the marked inhibitory effects on the frequency of rhythmic bladder contractions. Especially, the effects of the compounds of Examples 1 and 2 were about 8 times more potent than that of inaperisone hydrochloride (Compound A). In addition, the effects of the compounds of Examples 62, 68, 4, 36 and 43 were approximately 5.7, 4.7, 3, 3 and 3 times more potent in comparison with that of inaperisone hydrochloride, respectively.

Besides, the compounds of Examples 2, 3, 4, 12, 20, 26, 36, 41, 43–47, 49, 50, 56, 62, 68 and 72 not only exhibited the inhibition on the contractile frequency, but also suppressed the amplitude of contraction.

EXPERIMENT 2

Effect on the bladder contractions induced by stimulation of the pelvic nerve

Male Std-Wistar rats weighing 250–350 g were used. Under urethane anesthesia (1 g/kg, i.p.), both ureters were tied and cut at the side of kidney after a mid line incision of the abdomen. When the peripheral end of the pelvic nerve was stimulated, one side of the pelvic nerve was cut. When the central cut end of the nerve was stimulated, one side of the pelvic nerve was cut like in the peripheral end stimulation after both the hypogastric nerves were cut. Then, the bladder was exposed, the cannula connected to a syringe and a pressure transducer was inserted into the bladder via a small incision at an apex of the dome, and the proximal urethra was then ligated. Fifteen minutes after the operation, warm saline solution of an amount (0.1–0.2 ml) being small enough not to cause rhythmic contraction was infused into the bladder using a syringe. The change of the intravesical pressure was recorded on a recorder via a pressure transducer. The pelvic nerve was stimulated at the peripheral cut end or the central one by a pair of platinum electrodes with pulse of 1 msec duration, 3 v strength and a frequency of 10 Hz (for peripheral) or 5 v strength and a frequency of 20 Hz (for central), for 5 seconds every 2 minutes. Test compounds dissolved in distilled water were injected at a dose of 5 mg/kg via the cannula inserted into the jugular vein.

Table 4 shows the inhibitory rate of test compounds on the contractions at 2, 4, 10 and 20 minutes after the administration of test compound, which was calculated as compared with the control response before the administration of test compound, and was compared with that of vehicle (distilled water)-treated group (unpaired t-test). Each value in the table is mean±standard error of mean in 3–4 animals.

TABLE 4

Effect on the bladder contractions induced by stimulation of the pelvic nerve

| Test Comp. | Inhibitory rate (%) on the contraction caused by the stimulation of the peripheral cut end | | | |
|---|---|---|---|---|
| | 2 min. | 4 min. | 10 min. | 20 min. |
| Control | −4.1 ± 7.4 | −2.4 ± 7.5 | 3.0 ± 5.0 | 6.6 ± 8.1 |
| Ex. 1 | 4.4 ± 4.4 | 3.4 ± 4.4 | 3.2 ± 7.5 | 9.6 ± 8.6 |
| Ex. 2 | 0.4 ± 5.2 | 16.3 ± 7.0 | 13.7 ± 4.5 | 19.0 ± 7.5 |
| Ex. 43 | 2.4 ± 3.3 | 5.8 ± 6.3 | 6.3 ± 8.1 | 17.2 ± 12.2 |
| Comp. A | 6.2 ± 5.1 | 14.7 ± 4.0 | 25.1 ± 4.2* | 31.6 ± 2.5* |
| Control | −8.1 ± 5.0 | −1.4 ± 5.1 | −1.5 ± 11.6 | 1.7 ± 9.2 |
| Ex. 1 | 26.3 ± 10.0* | 27.6 ± 5.6** | 36.8 ± 10.1 | 44.1 ± 5.8** |
| Ex. 2 | 13.3 ± 5.1* | 17.7 ± 2.8* | 25.6 ± 3.7** | 24.9 ± 4.1 |
| Ex. 43 | 6.0 ± 10.8 | 22.8 ± 9.7 | 28.3 ± 4.0 | 37.3 ± 5.0* |
| Comp. A | 21.0 ± 10.7* | 22.5 ± 7.3* | 29.3 ± 7.7 | 40.6 ± 8.8* |

[note]:
*: $p<0.05$,
**: $<0.01$ (compared with the control group, student t-test)

As is clear from Table 4, the effects of the compounds of Examples 1, 2 and 43 on the bladder contractions induced by the stimulation of central cut end were more potent than those on the contractions induced by the stimulation of peripheral cut end. The result suggests that the effects of the compounds of the invention may be mediated mainly via the central nervous system.

EXPERIMENT 3

Inhibitory effect on exploratory behavior

Male Std-Wistar rats weighing 150–200 g were used in groups of 5 animals. One hour after oral administration of test compounds suspended in 0.5% aqueous tragacanth solution, animals were individually placed in a test cage (23×35×30 cm) on an Animex activity meter (Farad Co., Sweden). Immediately thereafter, locomotor counting was started and lasted for three minutes. The mean value of the exploratory behavior (count/3 minutes) in the test compound-treated groups were determined, and then inhibitory effect of each test compound was calculated as compared with that of the control group (0.5% aqueous tragacanth solution-treated group). The results are shown in Table 5 along with the results of Experiments 4 and 5.

EXPERIMENT 4

Inhibitory effect on polysynaptic spinal reflex

The experiment was performed according to the method of Itoh, et al. [Japan J. Parmacol.,23, 1125 (1982)]. Male Std-Wistar rats weighing 250–350 g were used in groups of 4–6 animals. Under anesthesia with combined i.p. injection of urethane (400 mg/kg) and α-chloralose (50 mg/kg), the rat fixed in a stereotaxic apparatus was clamped at the spine and tibial bane. A concentric needle electrode was inserted into the left gastrocnemius muscle, and the central end of the ipsilateral common peroneal nerve at the same side was supramaximally stimulated by an electrical stimulator (rectangular pulse,0.1 msec,0.1 Hz). Test compounds dissolved in distilled water were injected via a cannula inserted into the right femoral vein, and the evoked electromyogram was periodically recorded (2, 5, 10, 20 and 30 minutes after the injection). Inhibitory effect of test compounds on the amplitude of evoked electromyogram was expressed as a percentage against the amplitude before the administration and then, $ID_{50}$ value (the dose required for 50% inhibition of the amplitude) was calculated according to the method of Litchfied-Wilcoxon on the basis of the maximum inhibitory rate at each dose. The results are shown in Table 5 along with the results of Experiments 3 and 5.

EXPERIMENT 5

Acute toxicity

Male ddY mice weighing 18–25 g were used in groups of 5–15 animals. Test compounds suspended in 0.5% aqueous tragacanth solution were given orally, and the mortality was investigated for 7 days following administration. $LD_{50}$ value (50% lethal dose) was calculated according to the method of Litchfield-Wilcoxon. The results are shown in Table 5 along with the results of Experiments 3 and 4.

TABLE 5

Inhibitory effect on exploratory behavior, inhibitory effect on polysynaptic spinal reflex and acute toxicity

| Test Comp. | Inhibitory effect on exploratory behavior | | Inhibitory effect on polysynaptic spinal reflex $ID_{50}$ (i.v.) | Acute toxicity $LD_{50}$ (p.o.) |
|---|---|---|---|---|
| | Dose (p.o.) | Inhibitory rate (%) | | |
| Ex. 1 | 500 mg/kg | 16.2% | >10 mg/kg | 556 mg/kg |
| Ex. 2 | 500 mg/kg | 0% | >8 mg/kg | 620 mg/kg |
| Ex. 43 | 500 mg/kg | 20.0% | 3.82 mg/kg | 1043 mg/kg |
| Comp. A | 500 mg/kg | 28.3% | 4.22 mg/kg | 458 mg/kg |

As is clear from Table 5, the inhibitory effects of the compounds of Examples 1 and 2 on exploratory behavior were less potent than that of Compound A, and the inhibitory effect of the compound of Example 43 on exploratory behavior was almost equal to that of Compound A. In the experiment of spinal reflex, the inhibitory effect of the compound of Example 43 was nearly equal to that of Compound A, but the effects of the compounds of Examples 1 and 2 were much weaker than that of Compound A. The acute toxicity of the compound of Example 43 was about twice lower than that of Compound A, and those of the compounds of Examples 1 and 2 were also lower than that of Compound A.

Judging as a whole from these results and the results of Experiment 1, the inhibitory effects of the compounds of Examples 1, 2 and 43 on rhythmic bladder contractions (micturition reflex) are extremely separated from side effects such as central depression and inhibition of spinal reflex, and toxicity, in comparison with those of Compound A.

As is clear from the above results, the compound of the formula (I), a pharmaceutically acceptable acid addition salt thereof, and an N-oxide derivative thereof (hereinafter, occasionally referred to as "the compound of the present invention") exhibit a potent inhibitory effect on the micturition reflex, and show low toxicity, and hence, these compounds are useful as an agent for treatment of frequent urination and urinary incontinence, particularly for a remedy for treatment of various diseases caused by the decrease of the bladder volume capacity (e.g., unstable bladder, neurogenic bladder, chronic cystitis, chronic prostatitis, and nervous pollakisuria), which are induced by various factors.

The compounds of the present invention can be administered either orally, parenterally or rectally, but the oral administration is preferable. The dose of the compounds of the present invention may vary in accordance with, for example, the kinds of the compounds, the administration routes, and the conditions and ages of the patients, but it is usually in the range of 0.1–20 mg/kg/day, preferably in the range of 0.4–10 mg/kg/day, which is administered once a day or divided into several units.

The compounds of the present invention is usually administered in the form of a pharmaceutical composition which is prepared by mixing the active compounds with a pharmaceutically acceptable carrier or diluent. The pharmaceutically acceptable carrier or diluent may be any conventional ones which are usually used in the pharmaceutical field, and do not react with the compounds of the present invention. Suitable examples of the pharmaceutically acceptable carrier or diluent are, for example, lactose, inositol, glucose, mannitol, dextran, starch, partially pregelatinized starch, sucrose, magnesium alumino-silicate, synthetic aluminum silicate, crystalline cellulose, sodium carboxymethylcellulose, hydroxypropyl starch, calcium carboxymethylcellulose, ion exchange resin, methylcellulose, gelatin, gum arabic, hydroxypropylcellulose, low substituted hydroxypropylcellulose, hydroxypropylmethylcellulose, polyvinyl-pyrrolidone, polyvinyl alcohol, alginic acid, sodium alginate, light anhydrous silicic acid, magnesium stearate, talc, carboxyvinyl polymer, titanium oxide, sorbitan fatty acid esters, sodium lauryl sulfate, glycerin, glycerin fatty acid esters, purified lanolin, glycerogelatin, polysorbate, macrogol, vegetable oils, wax, liquid paraffin, white petrolatum, nonionic surfactants, propylene glycol, and water.

The pharmaceutical composition is, for example, tablets, capsules, granules, powders, syrups, suspensions, suppositories, cataplasms, and injection preparations. These preparations may be prepared by a conventional method. In the preparation of liquids, the compound of the present invention may be dissolved or suspended in water or a suitable other solvent, when administered. Tablets and granules may be coated by a conventional method.

These pharmaceutical compositions may contain the compound of the present invention at a ratio of more than 0.1%, preferably at a ratio of 1–70%. These pharmaceutical compositions may also contain other therapeutically effective compounds as well.

BEST MODE FOR CARRYING OUT THE INVENTION

The present invention is illustrated in more detail by the following Examples and Reference Examples, but should not be construed to be limited thereto.

The identification of the compounds is carried out by Elementary analysis, Mass spectrum, IR spectrum, NMR spectrum, etc.

The following abbreviations may be used in the following Examples and Reference Examples in order to simplify the description.

Me: Methyl group
Et: Ethyl group
Ph: Phenyl group
Fu: Fumaric acid
MA: Maleic acid
OX: Oxalic acid
A: Ethanol
AC: Acetone
AN: Acetonitrile
DE: Diethyl ether
EM: Ethyl methyl ketone
IP: Isopropyl alcohol

EXAMPLE 1

Preparation of 1-[2-(5-fluoro-3,4-dihydro-2-naphthalenyl)ethyl]-pyrrolidine

To a solution of 5-fluoro-1,2,3,4-tetrahydro-2-[2-(1-pyrrolidinyl)ethyl]-1-naphthalenol (20.0 g) in toluene (250 ml) was added p-toluenesulfonic acid. monohydrate (16.2 g), and the mixture was refluxed overnight. After cooling, the reaction solution was washed successively with 1N aqueous sodium hydroxide solution, water and a saturated sodium chloride solution, and dried over anhydrous sodium sulfate, and concentrated under reduced pressure. The residue was purified by silica gel column chromatography (eluent; toluene:ethyl acetate=5:1), and the fractions containing the desired compound were combined, concentrated under reduced pressure to give the desired compound (12.6 g), as an oily product.

The above obtained free base was dissolved in a 30% solution of hydrogen chloride in ethanol (100 ml), and the mixture was concentrated under reduced pressure to remove the ethanol. To the residue was added diethyl ether, and the precipitated crystals were collected by filtration, and recrystallized from acetonitrile to give a hydrochloride of the desired compound (4.5 g), m.p. 194°–198° C.

EXAMPLE 2

Preparation of 1-[2-(3,4-dihydro-6,7-dimethyl-2-naphthalenyl)ethyl]-pyrrolidine 1,2,3,4-Tetrahydro-6,7-dimethyl-2-[2-(1-pyrrolidinyl) ethyl]-1-naphthalenol (24.0 g) was dissolved in a 30% solution of hydrogen chloride in ethanol (240 ml), and the mixture was refluxed for one hour. The reaction solution was concentrated under reduced pressure, and the residue was dissolved in water. The mixture was basified with potassium carbonate, and extracted with ethyl acetate. The extract was washed with water and a saturated aqueous sodium chloride solution, dried over anhydrous sodium sulfate, and concentrated under reduced pressure to remove the solvent. The residue was purified by silica gel column chromatography (eluent; chloroform:methanol=10:1), and the fractions containing the desired compound were combined, and concentrated under reduced pressure to give the desired compound (14.5 g) as an oily product.

The above obtained free base was treated with a 30% solution of hydrogen chloride in ethanol in the same manner as in Example 1 to give a hydrochloride thereof, which was further recrystallized from ethanol to give a hydrochloride of the desired compound, m.p. 212°–214° C.

$^1$H-NMR spectrum (200 MHz, $(CD_3)_2SO$, δppm) :1.75–2.08 (m,4H), 2.10–2.27 (m,2H), 2.14 (s,6H), 2.53–2.77 (m,4H), 2.83–3.15 (br s,2H), 3.15–3.39 (m, 2H), 3.39–3.68 (br s,2H), 6.24 (s,1H), 6.79 (s,1H), 6.88 (s,1H), 10.85 (br s,1H)

EXAMPLES 3–41

The corresponding 1,2,3,4-tetrahydro-2-[ω-(1-cyclic amino)alkyl]-1-naphthalenols were treated in the same manner as in Example 1 or 2 to give the compounds as listed in Table 6. 1,2,3,4-Tetrahydro-2-[ω-(1-cyclic amino)alkyl]-1-naphthalenols were prepared by treating the corresponding 1-[ω-(1,2,3,4-tetrahydro-1-oxo-2-naphthalenyl)alkanoyl] cyclic amines which were obtained in Reference Examples 4–7, in the same manner as in Reference Example 8.

TABLE 6

Structure: naphthalene derivative with $R^1$ at position 8, $R^2$ at position 7/6, $R^3$ at position 5, with substituent $-(CH_2)_p-N$ cyclic $(CH_2)_q$ at position 2. ·Q

| Ex. No. | $R^1$ | $R^2$ | p | q | Q | m.p. (°C.) | Solv. for re-crystal. |
|---|---|---|---|---|---|---|---|
| 3 | H | H | 3 | 5 | MA | 105–106 | IP |
| 4 | H | H | 4 | 4 | HCl | 142–144 | AN |
| 5 | H | H | 4 | 4 | FU | 125–128 | AN |
| 6 | H | H | 4 | 5 | OX | 151–153 | A |
| 7 | H | H | 5 | 5 | OX | 144–145 | A |
| 8 | H | 5-F | 2 | 5 | MA.¾ H$_2$O | 120–121 | IP |
| 9 | H | 5-F | 2 | 6 | HCl | 201–205 | AN |
| 10 | H | 6-F | 2 | 4 | HCl | 181–185 | A−AC |
| 11 | H | 6-F | 2 | 5 | MA.½ H$_2$O | 118–119 | IP |
| 12 | H | 7-F | 2 | 5 | HCl.³⁄₂₀ H$_2$O | 207–209 | IP |
| 13 | H | 7-F | 2 | 5 | MA.½ H$_2$O | 106–107 | IP |
| 14 | H | 5-Cl | 2 | 4 | HCl | 168–169 | EM |
| 15 | H | 7-Cl | 2 | 4 | HCl | 223–227 | EM |
| 16 | H | 7-Cl | 2 | 5 | MA | 127–129 | AN |
| 17 | H | 5-Me | 2 | 4 | HCl | 182–184 | EM |
| 18 | H | 5-Me | 2 | 5 | MA | 170–171 | A |
| 19 | H | 6-Me | 2 | 5 | MA | 107–108 | IP |
| 20 | H | 7-Me | 2 | 4 | MA | 92–93 | IP |
| 21 | H | 7-Me | 2 | 5 | MA | 134–136 | IP |
| 22 | H | 7-Et | 2 | 4 | HCl | 196–198 | EM |
| 23 | H | 7-Et | 2 | 5 | OX | 175–177 | A |
| 24 | H | 5-OMe | 2 | 4 | MA | 117–119 | IP |
| 25 | H | 5-OMe | 4 | 4 | FU | 208–214 | AN |
| 26 | H | 5-OMe | 2 | 5 | MA | 131–132 | IP |
| 27 | H | 5-OEt | 2 | 4 | HCl | 182–186 | AN |
| 28 | H | 5-OEt | 2 | 5 | MA | 158–160 | A |
| 29 | H | 5-OMe | 2 | 6 | OX | 172–174 | A |
| 30 | H | 5-OMe | 3 | 5 | OX | 132–134 | A |
| 31 | H | 5-OMe | 4 | 5 | MA | 109–110 | A |
| 32 | H | 5-OMe | 5 | 5 | OX | 135–140 | A |
| 33 | H | 6-OMe | 2 | 5 | MA | 116–117 | IP |
| 34 | H | 7-OMe | 2 | 5 | OX | 179–180 | A |
| 35 | H | 5-OH | 2 | 5 | MA | 151–152 | EM |
| 36 | 7-F | 6-F | 2 | 4 | HCl | 198–201 | EM |
| 37 | 7-Cl | 6-Cl | 2 | 4 | HCl | 229–230 | EM |
| 38 | 7-OEt | 6-F | 2 | 5 | HCl | 205–210 | AN |
| 39 | 7-Me | 5-Me | 2 | 4 | HCl.¹⁄₁₀ H$_2$O | 178–182 | AN |
| 40 | 7-Me | 5-Me | 2 | 5 | HCl.⅕ H$_2$O | 229–233 | AN |
| 41 | 7-Me | 6-Me | 2 | 3 | MA | 116–119 | AN |
| 42 | 7-Me | 6-Me | 2 | 5 | MA | 157–158 | IP |
| 43 | 7-Me | 6-Me | 2 | 5 | HCl | 244–246 | AN |
| 44 | 7-Me | 6-Me | 2 | 6 | HCl | 238–240 | AN |
| 45 | 7-Me | 6-Me | 2 | 7 | HC.¹⁄₁₀ H$_2$O | 208–213 | AN |
| 46 | 7-Et | 6-Et | 2 | 4 | FU | 108–111 | AN |
| 47 | 7-(CH$_2$)$_3$-6 | | 2 | 4 | FU | 178–183 | AN |
| 48 | 7-(CH$_2$)$_3$-6 | | 2 | 5 | MA | 155–157 | A |
| 49 | 7-OCH$_2$O-6 | | 2 | 4 | HCl | 207–212 | EM |

EXAMPLE 50

Preparation of 1-[2-(3,4-dihydro-6,7-dimethyl-2-naphthalenyl)ethyl]-2,5-dimethylpyrolidine 1,2,3,4-Tetrahydro-6,7-dimethyl-1-oxo-2-naphthalenyl) acetyl]-2,5-dimethylpyrrolidine was treated in the same manner as in Reference Example 8 to give 1,2,3,4-tetrahydro-6,7-dimethyl-2-[2-(2,5-dimethyl-1-pyrrolidinyl) ethyl]-1-naphthalenol as an oily product, which was further treated in the same manner as in Example 2 to give a hydrochloride of the desired compound, m.p. 227°–229° C. (recrystallized from acetonitrile).

EXAMPLE 51

Preparation of 1-[2-(3,4-dihydro-6,7-dimethyl-2-naphthalenyl)ethyl]-2-(methoxymethyl)pyrrolidine 1-[(1,2,3,4-Tetrahydro-6,7-dimethyl-1-oxo-2-naphthalenyl)acetyl]-2-(methoxymethyl)pyrrolidine was treated in the same manner as in Reference Example 8 to give 1,2,3,4-tetrahydro-6,7-dimethyl-2-[2-(2-(methoxymethyl)-1-pyrrolidinyl)ethyl]-1-naphthalenol as an oily product, which was further treated in the same manner as in Example 1 to give a fumarate of the desired compound, m.p. 166°–168° C. (recrystallized from acetonitrile).

EXAMPLE 52

Preparation of 1-[2-(5,7-difluoro-3,4-dihydro-2-naphthalenyl)ethyl]-pyrrolidine

To the borane complex with.5,7-difluoro-1,2,3,4-tetrahydro-2-[2-(1-pyrrolidinyl)ethyl]-1-naphthalenol, which was obtained in the following Reference Example 9, were added p-toluenesulfonic acid monohydrate (4.1 g) and toluene (54 ml), and the mixture was refluxed for three hours. After cooling, the reaction solution was washed with 10% aqueous sodium hydroxide solution, dried over anhydrous sodium sulfate, and concentrated under reduced pressure to remove the solvent. The residue was purified by silica gel column chromatography (eluent; chloroform:methanol= 50:1), and the fractions containing the desired compound were combined and concentrated under reduced pressure to give the desired compound (2.0 g) as an oily product. The product thus obtained was treated with oxalic acid in ethanol in the conventional manner to give an oxalate thereof, which was further recrystallized from acetonitrile to give an oxalate of the desired compound, m.p. 146°–149° C.

The borane complex with 5-fluoro-1,2,3,4-tetrahydro-2-[2-(1-pyrrolidinyl)-ethyl]-1-naphthalenol, which was obtained in the following Reference Example 12, was treated in the same manner as in the above Example to give the compound of Example 1.

EXAMPLES 53–57

The borane complexes with the corresponding.1,2,3,4-tetrahydro-2-[2-(1-pyrrolidinyl)ethyl]-1-naphthalenol, which were obtained in the same manner as in Reference Example 9 described below, were treated in the same manner as in Example 52 to give the compounds as listed in Table 7.

TABLE 7

$R^1$, $R^2$, $R^3$, $(CH_2)_2-N$, $R^4$, .Q

| Ex. No. | $R^1$ | $R^2$ | $R^4$ | Q | m.p. (°C.) | Solv. for recrystal |
|---|---|---|---|---|---|---|
| 53 | H | 5-F | F | HCl | 203–205 | EM |
| 54 | 6-F | 5-F | H | HCl | 202–204 | EM |
| 55 | 8-F | 5-F | H | OX | 161–165 | AN |
| 56 | H | 7-COOMe | H | HCl | 191–192 | EM |
| 57 | 7-Me | 6-Me | F | HCl | 204–206 | EM |

EXAMPLE 58

Preparation of 1-[2-(3,4-dihydro-7-methoxy-2-naphthalenyl)ethyl]-pyrrolidine

To 3,4-dihydro-7-methoxy-2-naphthalenethyl methanesulfonate, which was obtained in Reference Example 10 described below, were added acetonitrile (70 ml) and pyrrolidine (3.5 g), and the mixture was refluxed for six hours. The mixture was concentrated under reduced pressure to remove the solvent, and the residue was purified by silica gel column chromatography (eluent; chloroform:methanol=50:1). The fractions containing the desired compound ware combined, and concentrated under reduced pressure to give the desired compound (2.5 g) as an oily product.

The above obtained free base was treated with a 30% solution of hydrogen chloride in ethanol in the same manner as in Example 1 to give a hydrochloride thereof, which was further recrystallized from ethyl methyl ketone to give a hydrochloride of the desired compound, m.p. 161°–163° C.

EXAMPLES 59–61

The corresponding 3,4-dihydro-2-naphthalenethyl methanesulfonates, which ware obtained in the same manner as in Reference Example 10 described below, were treated in the same manner as in Example 58 to give the following compounds.

(EXAMPLE 59)

1-[2-(3,4-Dihydro-2-naphthalenyl)ethyl]pyrrolidine hydrochloride, m.p. 205°–207° C. (recrystallized from ethanol-diethyl ether)

(EXAMPLE 60)

1-[2-(3,4-Dihydro-2-naphthalenyl)ethyl]-3-hydroxypyrrolidine hydrochloride, m.p. 126°–128° C. (recrystallized from ethyl methyl ketone)

(EXAMPLE 61)

3-Fluoro-1-[2-(3,4-dihydro-6,7-dimethoxy-2-naphthalenyl)ethyl]-pyrrolidine hydrochloride, m.p. 202°–205° C. (recrystallized from ethyl methyl ketone)

EXAMPLE 62

Preparation of 1-[2-(3,4-dihydro-6,7-dimethoxy-2-naphthalenyl)ethyl]-pyrrolidine To 1,2,3,4-tetrahydro-2-(2-methanesulfonyloxyethyl)-6,7-dimethoxy-1-naphthalenyl methanesulfonate, which was obtained in Reference Example 11 described below, were added acetonitrile (72 ml) and pyrrolidine (4.5 g), and the mixture was refluxed for six hours. The mixture was concentrated under reduced pressure to remove the solvent, and the residue was purified by silica gel column chromatography (eluent; chloroform:methanol=50:1). The fractions containing the desired compound were combined, and concentrated under reduced pressure to give the desired compound (3.5 g) as an oily product.

The above obtained free base was treated with a 30% solution of hydrogen chloride in ethanol in the same manner as in Example 1 to give a hydrochloride thereof, which was further recrystallized from ethyl methyl ketone to give a hydrochloride of the desired compound, m.p. 204°–206° C.

EXAMPLES 63–70

The corresponding 1,2,3,4-tetrahydro-2-(2-methanesulfonyloxyethyl)-1-naphthalenyl methanesulfonates, which were obtained in the same manner as in Reference Example 11 described below, were treated in the same manner as in Example 62 to give the compounds as listed in Table 8. The solvent for recrystallization is diethyl ether for the compound of Example 63, and ethyl ketone for the compounds of all of the remaining Examples.

TABLE 8

| Ex. No. | $R^1$ | $R^2$ | $R^3$ | $R^4$ | $R^5$ | Q | m.p.(°C.) |
|---|---|---|---|---|---|---|---|
| 63 | H | 5-F | H | OH | H | — | 74–78 |
| 64 | 6-OMe | H | H | H | H | HCl | 225–227 |
| 65 | H | H | 7-Ph | H | H | HCl | 194–196 |
| 66 | 7-Me | 6-Me | H | OH | H | HCl | 191–194 |
| 67 | 7-Me | 6-Me | H | F | F | HCl | 207–209 |
| 68 | 7-OMe | 6-Me | H | H | H | HCl | 220–221 |
| 69 | 7-OCH$_2$CH$_2$-6 | | H | H | H | HCl | 206–209 |
| 70 | 8-OMe | 7-OMe | 6-OMe | H | H | HCl | 184–186 |

EXAMPLE 71

Preparation of 1-[2-(3,4-dihydro-7-hydroxymethyl-2-naphthalenyl)ethyl]-pyrrolidine 1-[2-(3,4-Dihydro-7-methoxycarbonyl-2-naphthalenyl) ethyl]pyrrolidine (1.0 g) was dissolved in tetrahydrofuran (20 ml), and thereto was added dropwise a 1.5M solution of diisobutyl aluminum hydride in toluene (7.0 ml) under ice-cooling, and the mixture was stirred for one hour. To the reaction solution was added dropwise water to decompose the excess amount of the reducing agent, and the mixture was extracted with ethyl acetate. The extract was dried over anhydrous sodium sulfate, and concentrated under reduced pressure to remove the solvent. The residue was purified by silica gel column chromatography (eluent; chloroform:methanol=30:1), and the fractions containing the desired compound were combined, and concentrated under reduced pressure to give the desired compound (0.8 g) as an oily product.

The above obtained free base was treated with a 30% solution of hydrogen chloride in ethanol in the same manner as in Example 1, to give a hydrochloride thereof, which was further recrystallized from ethyl methyl ketone to give a hydrochloride of the desired compound, m.p. 193°–194° C.

$^1$H-NMR spectrum (200 MHz, CDCl$_3$, δ ppm):1.72 (m,1H),1.95–2.20(m, 4H),2.27(t,2H, J=8.5),2.72–2.91(m, 6H),3.15–3.29(m,2H),3.75–3.94(m,2H) 4.55(d,2H, J=5), 6.28(s,1H),7.01(s,1H),7.05–7.17(m,2H),12.65(m,1H)

EXAMPLE 72

Preparation of 1-[2-(3,4-dihydro-6-hydroxymethyl-7-methyl-2-naphthalenyl)ethyl]pyrrolidine 1-[2-(3,4-Dihydro-6-methoxycarbonyl-7-methyl-2-naphthalenyl)ethyl]-pyrrolidine was treated in the same manner as in Example 71 to give the desired compound, m.p. 76°–77° C. (recrystallized from diethyl ether-hexane).

EXAMPLE 73

Preparation of 1-[2-(7-carboxy-3,4-dihydro-2-naphthalenyl)ethyl]-pyrrolidine

1-[2-(3,4-Dihydro-7-methoxycarbonyl-2-naphthalenyl) ethyl]pyrrolidine (1.0 g) was dissolved in ethanol (5 ml), and thereto was added 1N aqueous sodium hydroxide solution (5.2 ml), and the mixture was stirred at 25° C. for 6 hours. The mixture was concentrated under reduced pressure to remove the solvent, and the residue was acidified with 10% hydrochloric acid. The precipitated crystals were collected by filtration, and subjected to desalting with using CHP-20P [manufactured by Mitsubishi Kasei Corporation, high porous polystyrene resin; 75–150 μm] (eluent; water, then acetonitrile). The eluents were concentrated under reduced pressure, and the residue was recrystallized from ethanol-ethyl methyl ketone to give the desired compound, m.p. 202°–203° C.

$^1$H-NMR spectrum (200 MHz, (CD$_3$)$_2$SO, δppm) :1.80–2.10(m,4H),2.28(t,2H, J=7),2.62(t,2H, J=8),2.85(t, 2H, J=8),2.90–3.12(m,2H), 3.32(t,2H,J=7),3.41–3.65(m, 2H),6.44(s,1H),7.25(d,1H, J=8),7.60(d,1H, J=1),7.70(dd, 1H, J=8, 1),10.56(m,1H),12.80(m,1H)

EXAMPLE 74

Preparation of 1-[2-(6-carboxy-3,4-dihydro-7-methyl-2-naphthalenyl)-ethyl]pyrrolidine 1-[2-(3,4-Dihydro-6-methoxycarbonyl-7-methyl-2-naphthalenyl)ethyl]-pyrrolidine was treated in the same manner as in Example 73 to give a hydrochloride of the desired compound, m.p. 258°–259° C. (recrystallized from ethanol-ethyl methyl ketone).

The starting compounds used in the above Examples were prepared as follows.

Reference Example 1

Preparation of 1,2,3,4-tetrahydro-6,7-dimethyl-1-oxo-2-naphthaleneacetic acid:

(1) A mixture of 37% formalin (18 g) and dimethylamine hydrochloride (18 g) was stirred at 25° C. for 30 minutes, and stirred at 70° C. for 30 minutes. The reaction temperature was raised to 80° C., and to the mixture was added dropwise acetic anhydride (80 ml). The reaction mixture was stirred at 80° C. for one hour, and thereto was added 3,4-dihydro-6,7-dimethyl-1(2H)-naphthalenone (26 g). The reaction temperature was raised to 90° C., and the mixture was stirred for 6 hours. The mixture was concentrated under reduced pressure to remove the solvent, and to the residue was added acetone. The precipitated crystals were collected by filtration, and washed with acetone to give 2-dimethylaminomethyl-3,4-dihydro-6,7-dimethyl-1(2H)-naphthalenone hydrochloride (39 g).

(2) The above obtained Mannich base hydrochloride (39 g) was dissolved in ice-water, and the mixture was basified with aqueous ammonia, and extracted with dichloromethane. The dichloromethane layer was washed with water, and dried over anhydrous magnesium sulfate, and the resultant was concentrated under reduced pressure at a temperature below 40° C. to remove the solvent. The residue was dissolved in acetone, and thereto was added dropwise methyl iodide (10.8 ml) with stirring under ice-cooling. The mixture was further stirred for 30 minutes under ice-cooling, and then warmed to 25° C. The mixture was stirred for two hours. The crystals were collected by filtration, and washed with acetone to give 1,2,3,4-tetrahydro-N,N,N,6,7-pentamethyl-1-oxo-2-naphthalene-methanaminium iodide (46 g).

(3) The above obtained quaternary salt (46 g) was dissolved in methanol (300 ml), and thereto was added a solution of potassium cyanide (9.6 g) in water (80 ml), and the mixture was stirred at 25° C. for three hours. The reaction mixture was concentrated under reduced pressure, and the residue was extracted with ethyl acetate. The ethyl acetate layer was washed with water and a saturated aqueous sodium chloride solution, and dried over anhydrous magnesium sulfate. The resultant was concentrated under reduced pressure to remove the solvent to give 1,2,3,4-tetrahydro-6,7-dimethyl-1-oxo-2-naphthalene-acetonitrile (22 g) as crystals.

(4) The above acetonitrile compound (22 g) was dissolved in a mixture of conc. hydrochloric acid (200 ml) and glacial acetic acid (200 ml), and the mixture was refluxed for 6 hours. To the reaction solution was added water, and the precipitated crystals were collected by filtration, washed with water, and recrystallized from ethyl methyl ketone to give the desired compound (16.5 g), m.p. 193°–194° C.

IR spectrum (KBr, cm$^{-1}$):1707, 1676

$^1$H-NMR spectrum (200 MHz, CDCl$_3$, δppm):1.81–2.24 (m,2H),2.27(s, 3H),2.29(s,3H),2.38–2.56(m,1H),2.89–3.15 (m,4H),7.02(s,1H),7.80(s,1H),10.50(br s,1H)

Reference Example 2

Preparation of 1,2,3,4-tetrahydro-1-oxo-2-naphthalenepropanoic acid (1) To a solution of diisopropylamine (16 ml) in tetrahydrofuran (350 ml) was added dropwise a 1.6M solution of butyl lithium in hexane (71 ml) under cooling at −78° C., and the mixture was stirred for 30 minutes. To the reaction mixture was added dropwise a solution of 3,4-dihydro-1 (2H)-naphthalenone (16.5 g) in tetrahydrofuran (60 ml) over a period of about 20 minutes under cooling at −78° C., and the mixture was stirred for 30 minutes. To the mixture was added dropwise a solution of ethyl 3-bromopropanoate (20.5 g) in tetrahydrofuran (60 ml) over a period of about 20 minutes, and then further stirred for 30 minutes. The reaction mixture was stirred overnight at 20° C., and diluted with diethyl ether. The mixture was washed successively with water,5% aqueous sodium hydrogen carbonate solution, and 5% hydrochloric acid, and dried over anhydrous magnesium sulfate. The resultant was concentrated under reduced pressure to remove the solvent to give ethyl 1,2,3,4-tetrahydro-1-oxo-2-naphthalene-propanoate (10.1 g) as an oily product.

(2) The above obtained ethyl ester compound (10.1 g) was dissolved in ethanol (200 ml), and thereto was added 2N aqueous sodium hydroxide solution (170 ml), and the mixture was refluxed for three hours. The mixture was concentrated under reduced pressure to remove the ethanol, and the aqueous layer was acidified with conc. hydrochloric acid, and extracted with dichloromethane. The dichloromethane layer was washed with water, dried over anhydrous magnesium sulfate, and concentrated under reduced pressure to remove the solvent. The residue was purified by silica gel column chromatography (eluent; chloroform), and the fractions containing the desired compound were combined, and concentrated under reduced pressure to give the desired compound (6.3 g) as an oily product.

The corresponding starting compounds were treated in the same manner as in the above Reference Example to give 1,2,3,4-tetrahydro-5-methoxy-1-oxo-2-naphthalenepropanoic acid as an oily product.

Reference Example 3

Preparation of 1,2,3,4-tetrahydro-1-oxo-2-naphthalenebutanoic acid (1) To a solution of diethyl carbonate (200 g) in toluene (800 ml) was added 60% sodium hydride (27.4 g), and the mixture was stirred at 50° C. for 30 minutes, and thereto was added dropwise a solution of 3,4-dihydro-1(2H)-napthalenone (50 g) in toluene (200 ml). The mixture was refluxed for one hour, and poured into ice-water, and the mixture was neutralized with acetic acid. The toluene layer was collected, washed successively with an aqueous potassium carbonate solution and water, dried over anhydrous magnesium sulfate, and concentrated under reduced pressure. The residue was purified by distillation under reduced pressure to give ethyl 1,2,3,4-tetrahydro-1-oxo-2-naphthalenecarboxylate (47 g) as an oily product, b.p. 135°–145° C./2 mmHg.

(2) The above obtained ethyl carboxylate compound (32 g) was dissolved in tert-butanol (120 ml), and thereto was added potassium tert-butoxide (25 g), and the mixture was refluxed for 30 minutes. The mixture was allowed to stand for cooling to 25° C., and thereto was added ethyl 4-bromobutanoate (34 g). The mixture was refluxed overnight, and concentrated under reduced pressure. To the residue was added water, and the mixture was extracted with diethyl ether. The ether layer was washed with water, dried over anhydrous magnesium sulfate, and concentrated under reduced pressure to give ethyl 2-ethoxy-carbonyl-1,2,3,4-tetrahydro-1-oxo-2-naphthalenebutanoate (50 g) as an oily product.

(3) The above obtained ethyl butanoate compound was dissolved in ethanol (500 ml), and thereto was added 30% aqueous potassium hydroxide solution (300 ml), and the mixture was refluxed overnight. The mixture was concentrated under reduced pressure to remove the ethanol, and the resultant was acidified with conc. hydrochloric acid, and extracted with dichloromethane. The dichloromethane layer was washed with water, dried over anhydrous magnesium sulfate, and concentrated under reduced pressure to remove the solvent to give the desired compound (23 g) as an oily product.

The corresponding starting compounds were treated in the same manner as in the above Reference Example to give the following compounds as an oily product.

1,2,3,4-tetrahydro-5-methoxy-1-oxo-2-naphthalenebutanoic acid, 1,2,3,4-tetrahydro-1-oxo-2-naphthalenepentanoic acid, and 1,2,3,4-tetrahydro-5-methoxy-1-oxo-2-naphthalenepentanoic acid.

Reference Example 4

Preparation of 1-[(1,2,3,4-tetrahydro-6-methyl-1-oxo-2-naphthalenyl)-acetyl]piperidine 1,2,3,4-Tetrahydro-6-methyl-1-oxo-2-naphthaleneacetic acid (7.0 g) and thionyl chloride (7 ml) were dissolved in chloroform (150 ml), and the mixture was refluxed for one hour. After cooling, the mixture was concentrated under reduced pressure to remove the solvent, and the residue was dissolved in toluene (100 ml), and thereto was added dropwise piperidine (8.2 g) under ice-cooling. The mixture was stirred at 25° C. for one hour, washed successively with dilute hydrochloric acid and water, dried over anhydrous magnesium sulfate, and concentrated under reduced pressure to remove the solvent. The residue was purified by silica gel column chromatography (eluent; toluene:ethyl acetate= 10:1), and the fractions containing the desired compound were combined and concentrated under reduced pressure to give the desired compound (4.4 g) as an oily product.

The corresponding staring compounds were treated in the same manner as in the above Reference Example to give 1-[(1,2,3,4-tetrahydro-7-methyl-1-oxo-2-naphthalenyl) acetyl]piperidine as an oily product.

Reference Example 5

Preparation of 1-[(1,2,3,4-tetrahydro-6,7-dimethyl-1-oxo-2-naphthalenyl)-acetyl]pyrrolidine To a solution of 1,2,3,4-tetrahydro-6,7-dimethyl-1-oxo-2-naphthalene-acetic acid (8.0 g), pyrrolidine (3.8 g) and benzotriazol-1-yloxy-tris(dimethyl-amino) phosphonium hexafluorophosphate (BOP Reagent,16.7 g) in dichloromethane (80 ml) was added dropwise triethylamine (3.8 g) at 25° C., and the mixture was stirred for three hours. The mixture was concentrated under reduced pressure to remove the solvent, and to the residue were added water and toluene, and the insoluble materials were removed by filtration. The toluene layer was collected, washed successively with 1N aqueous sodium hydroxide solution, water and a saturated aqueous sodium chloride solution, an dried over anhydrous sodium sulfate. The resultant was concentrated under reduced pressure to remove the solvent, and the residue was purified by silica gel column chromatography (eluent; toluene-ethyl acetate=10:1), and the fractions containing the desired compound were combined, and concentrated under reduced pressure to give the desired compound (9.5 g) as an oily product.

IR spectrum (neat, cm$^{-1}$):1672, 1638

$^1$H-NMR spectrum (200 MHz, CDCl$_3$, δ ppm):1.76–2.09 (m,5H),2.26(s, 3H),2.28(s,3H),2.17–2.40(m,2H),2.76–3.28 (m,4H),3.36–3.66 (m,4H), 7.00(s,1H),7.78(s,1H)

The 1,2,3,4-tetrahydro-1-oxo-naphthaleneacetic acids obtained in the same manner as in Reference Example 1 and the cyclic amine compounds were treated in the same manner as in Reference Example 5 to give the compounds as listed in Table 9.

TABLE 9

[Structure: tetrahydronaphthalenone with R¹ at position 8, R³ at position 5, and at position 2 a CH₂CON group attached to a cyclic (CH₂)q amine ring]

| R¹ | R² | q |
|---|---|---|
| H | 5-F | 4 |
| H | 5-F | 5 |
| H | 5-F | 6 |
| H | 6-F | 4 |
| H | 6-F | 5 |
| H | 7-F | 4 |
| H | 7-F | 5 |
| H | 5-Cl | 4 |
| H | 7-Cl | 4 |
| H | 7-Cl | 5 |
| H | 5-Me | 4 |
| H | 5-Me | 5 |
| H | 7-Me | 4 |
| H | 7-Et | 4 |
| H | 7-Et | 5 |
| H | 5-OMe | 4 |
| H | 5-OMe | 5 |
| H | 5-OEt | 4 |
| H | 5-OEt | 5 |
| H | 5-OMe | 6 |
| H | 6-OMe | 5 |
| H | 7-OMe | 5 |
| H | 5-OH | 5 |
| 7-F | 6-F | 4 |
| 7-Cl | 6-Cl | 4 |
| 7-OEt | 6-F | 5 |
| 7-Me | 5-Me | 4 |
| 7-Me | 5-Me | 5 |
| 7-Me | 6-Me | 3 |
| 7-Me | 6-Me | 5 |
| 7-Me | 6-Me | 6 |
| 7-Me | 6-Me | 7 |
| 7-Et | 6-Et | 4 |
| 7-(CH₂)₃-6 | | 4 |
| 7-(CH₂)₃-6 | | 5 |
| 7-OCH₂O-6 | | 4 |

Reference Example 6

The corresponding starting compounds were treated in the same manner as in Reference Example 5 to give the following compounds as an oily product.

1-[(1,2,3,4-tetrahydro-6,7-dimethyl-1-oxo-2-naphthalenyl)acetyl]-2,5-dimethylpyrrolidine, and 1-[(1,2,3,4-tetrahydro-6,7-dimethyl-1-oxo-2-naphthalenyl)acetyl]-2-(methoxymethyl)pyrrolidine.

Reference Example 7

Preparation of 1-[3-(1,2,3,4-tetrahydro-1-oxo-2-naphthalenyl)propanoyl]-piperidine To a solution of 1,2,3,4-tetrahydro-1-oxo-2-naphthalenepropanoic acid (6.3 g), piperidine (3.7 g) and BOP Reagent (15.4 g) in dichloromethane (150 ml) was added dropwise triethylamine (3.5 g) at 25° C., and the mixture was refluxed for three hours. The reaction mixture was washed successively with water and 10% hydrochloric acid, and dried over anhydrous magnesium sulfate. The resultant was concentrated under reduced pressure to remove the solvent, and the residue was purified by silica gel column chromatography (eluent; toluene:ethyl acetate=10:1), and the fractions containing the desired compound were combined, and concentrated under reduced pressure to give the desired compound (7.1 g) as an oily product.

The corresponding starting compounds were treated in the same manner as in the above Reference Example to give the following compounds.

1-[3-(1,2,3,4-tetrahydro-5-methoxy-1-oxo-2-naphthalenyl)propanoyl]-piperidine,

1-[4-(1,2,3,4-tetrahydro-1-oxo-2-naphthalenyl)butanoyl]pyrrolidine,

1-[4-(1,2,3,4-tetrahydro-1-oxo-2-naphthalenyl)butanoyl]piperidine,

1-[4-(1,2,3,4-tetrahydro-5-methoxy-1-oxo-2-naphthalenyl)butanoyl]-pyrrolidine,

1-[4-(1,2,3,4-tetrahydro-5-methoxy-1-oxo-2-naphthalenyl)butanoyl]-piperidine,

1-[5-(1,2,3,4-tetrahydro-1-oxo-2-naphthalenyl)pentanoyl]piperidine, and

1-[5-(1,2,3,4-tetrahydro-5-methoxy-1-oxo-2-naphthalenyl)pentanoyl]-piperidine.

Reference Example 8

Preparation of 1,2,3,4-tetrahydro-6,7-dimethyl-2-[2-(1-pyrrolidinyl)ethyl]-1-naphthalenol To a solution of 1-[(1,2,3,4-tetrahydro-6,7-dimethyl-1-oxo-2-naphthalenyl)acetyl]pyrrolidine (9.5 g) in toluene (100 ml) was added dropwise with stirring a 70% solution of sodium bis(2-methoxyethoxy)aluminum hydride in toluene (29.0 g) under ice-cooling, and the mixture was stirred at the same temperature for one hour, and stirred at 25° C. for three hours. The reaction mixture was cooled again with ice, and thereto was added dropwise a saturated aqueous sodium potassium tartrate solution (30 ml), and the mixture was stirred at the same temperature for 30 minutes in order to decompose the excess amount of the reducing agent. The organic layer was separated, washed successively with water and a saturated aqueous sodium chloride solution, dried over anhydrous sodium sulfate, and concentrated under reduced pressure to remove the solvent. The residue was purified by silica gel column chromatography (eluent; toluene:ethyl acetate=10:1), and the fractions containing the desired compound were combined, and concentrated under reduced pressure to give the desired compound (8.5 g) as an oily product.

IR spectrum (neat, cm$^{-1}$):3360, 3120

$^1$H-NMR spectrum (200 MHz, CDCl$_3$, δ ppm):1.46–1.95 (m,9H),2.20(s, 3H),2.23(s,3H),2.44–2.94(m,9H),4.31–4.41 (m,1H),6.81(s,1H),7.42(s,1H)

Reference Example 9

Preparation of 5,7-difluoro-1,2,3,4-tetrahydro-2-[2-(1-pyrrolidinyl)ethyl]-1-naphthalenol (1) A mixture of 5,7-difluoro-3,4-dihydro-1(2H)-naphthalenone (3.2 g), glyoxylic acid monohydrate (1.6 g) and 85% phosphoric acid (3 ml) was heated with stirring at 90° C. for four hours. After cooling, water was added to the reaction solution, and the precipitated crystals were collected by filtration, washed with water, and dried to give (5,7-difluoro-3,4-dihydro-1-oxo-2(1H)-naphthalenylidene) acetic acid (4.2).

$^1$H-NMR spectrum (200 MHz, CDCl$_3$, δ ppm):3.00(t,2H, J=7),3.40–3.60 (m,2H),6.91(t,1H, J=1),7.00–7.13(m,1H), 7.58–7.66(m,1H)

(2) To a solution of the above acetic acid compound (4.2 g), pyrrolidine (1.9 g) and BOP Reagent (8.6 g) in dichloromethane (40 ml) was added dropwise with stirring triethylamine (2.0 g) at 25° C., and the mixture was stirred for three hours. The mixture was concentrated under reduced pressure to remove the solvent, and to the residue were added water and toluene. The insoluble materials were removed by filtration, and the toluene layer was separated, washed successively with 1N aqueous sodium hydroxide solution, water, and a saturated aqueous sodium chloride solution, and dried over anhydrous sodium sulfate. The resultant was concentrated under reduced pressure to remove the solvent, and the residue was purified by silica gel column chromatography (eluent; toluene:ethyl acetate=2:1), and the fractions containing 1-[(5,7-difluoro-1,2,3,4-tetrahydro-1-oxo-2-naphthalenylidene)acetyl]pyrrolidine were combined, and concentrated under reduced pressure to give said amide compound (2.6 g) as an oily product.

$^1$H-NMR spectrum (200 MHz, CDCl$_3$, δ ppm):1.85–2.06 (m,4H),2.96(t, 2H, J=7),3.27–3.38(m,2H),3.48–3.67(m,4H),6.97–7.09(m,1H),7.16(t,1H,J=1),7.56–7.64(m,1H)

(3) The above obtained amide compound (2.6 g) was dissolved in ethanol (130 ml), and hydrogen gas was introduced through the mixture with stirring at 25° C. by using as a catalyst 10% palladium-carbon (0.3 g). After the theoretical amount of hydrogen gas was absorbed, the catalyst was removed by filtration. The filtrate was concentrated under reduced pressure to remove the solvent to give 1-[(5,7-difluoro-1,2,3,4-tetrahydro-1-oxo-2-naphthalenyl)acetyl]pyrrolidine (2.3 g) as an oily product.

$^1$H-NMR spectrum (200 MHz, CDCl$_3$, δ ppm):1.60(s,2H),1.80–2.08(m, 4H),2.28–2.41(m,1H),2.74–3.26(m,4H),3.40–3.58(m,4H),6.90–7.04(m,1H), 7.48–7.57(m,1H)

(4) The above product (2.3 g) was dissolved in tetrahydrofuran (23 ml), and thereto was added dropwise a 1M solution of borane-tetrahydrofuran complex in tetrahydrofuran (26 ml) under ice-cooling, and the mixture was stirred at 20° C. overnight. To the reaction solution was added dropwise methanol (26 ml) under ice-cooling, and the excess amount of the reducing agent was decomposed. The mixture was concentrated under reduced pressure to remove the solvent to give the desired compound in the form of a complex with borane.

Reference Example 10

Preparation of 3,4-dihydro-7-methoxy-2-naphthalenethyl methane-sulfonate (1) A mixture of 3,4-dihydro-7-methoxy-2(1H)-naphthalenone (5.0 g), benzoic acid (0.69 g), ethyl (triphenylphosphoranylidene)acetate (14.9 g) and toluene (20 ml) was refluxed overnight. After cooling, the insoluble materials were removed by filtration, and the filtrate was concentrated under reduced pressure. The residue was purified by silica gel column chromatography (eluent; hexane:ethyl acetate=10:1), and the fractions containing ethyl 3,4-dihydro-7-methoxy-2-naphthaleneacetate were combined, and concentrated under reduced pressure to give said ester compound (6.2 g) as an oily product.

(2) The above ester compound (4.9 g) was dissolved in anhydrous tetrahydrofuran (50 ml), and thereto was added dropwise a 1M solution of diisobutylaluminum hydride in toluene (48 ml) at −10° C., and the mixture was stirred at 0° C. for one hour. To the reaction solution was added dropwise water, and the excess amount of the reducing agent was decomposed. The insoluble materials were removed by filtration, and the filtrate was extracted with ethyl acetate. The organic layer was dried over anhydrous sodium sulfate, and concentrated under reduced pressure to remove the solvent to give 3,4-dihydro-7-methoxy-2-naphthalenethanol (3.5 g) as an oily product.

$^1$H-NMR spectrum (200 MHz, CDCl$_3$, δ ppm):1.65(br s,1H),2.25(t,2H, J=8.5),2.48(t,2H, J=7.5),2.75(t,2H, J=8.5),3.78(s,3H),3.75–3.84(m,2H), 6.29(s,1H),6.59(d,1H, J=3),6.66(dd,1H, J=8,3),7.01(d,1H, J=8)

(3) The above ethanol compound (3.5 g) and triethylamine (2.8 g) were dissolved in dichloromethane (70 ml), and thereto was added dropwise methane-sulfonyl chloride (2.2 g) at 0° C. The mixture was stirred at the same temperature for one hour, and concentrated under reduced pressure to remove the solvent to give the desired compound as an oily product.

Reference Example 11

Preparation of 1,2,3,4-tetrahydro-2-(2-methanesulfonyloxyethyl)-6,7-dimethoxy-1-naphthalenyl methanesulfonate (1) 3,4-Dihydro-6,7-dimethoxy-1(2H)-naphthalenone (10.0 g) was dissolved in tetrahydrofuran (200 ml), and thereto was added dropwise a 2M solution of lithium diisopropylamide in tetrahydrofuran (37 ml) at −70° C. The mixture was stirred for 30 minutes, and thereto was added dropwise ethyl bromoacetate (10.5 g) at −70° C. The mixture was stirred at the same temperature for two hours, and then stirred at 20° C. overnight. The reaction mixture was poured into ice-water, and extracted with diethyl ether. The ether layer was washed successively with water, 10% hydrochloric acid and 10% aqueous sodium hydrogen carbonate solution, and dried over anhydrous sodium sulfate. The resultant was concentrated under reduced pressure to remove the solvent to give ethyl 1,2,3,4-tetrahydro-6,7-dimethoxy-1-oxo-2-naphthaleneacetate (12.0 g) as an oily product.

(2) The above ester compound (12.0 g) was dissolved in toluene (100 ml), and thereto was added a 70% solution of sodium bis(2-methoxyethoxy)-aluminum hydride in toluene (24 g) under ice-cooling, and the mixture was stirred at 25° C. for 6 hours. To the reaction solution was added a saturated aqueous sodium potassium tartrate solution under ice-cooling, and the mixture was stirred for one hour. The organic layer was separated, dried over anhydrous sodium sulfate, and concentrated under reduced pressure to remove the solvent. The residue was purified by silica gel column chromatography (eluent; chloroform:methanol=20:1), and the fractions containing the 1,2,3,4-tetrahydro-2-(2-hydroxyethyl)-6,7-dimethoxy-1-naphthalenol were combined and concentrated under reduced pressure to give said diol compound (3.6 g) as an oily product.

$^1$H-NMR spectrum (200 MHz, CDCl$_3$, δ ppm):1.52–2.02 (m,5H),2.45–2.90(m,4H),3.71–3.95(m,2H),3.84(s,3H),3.89 (s,3H),4.44(d,1H, J=7),6.55(s,1H),7.05(s,1H)

(3) The above diol compound (3.6 g) and triethylamine (4.3 g) were dissolved in dichloromethane (72 ml), and thereto was added dropwise methanesulfonyl chloride (3.8 g) under ice-cooling. The mixture was stirred for one hour, and concentrated under reduced pressure to remove the solvent to give the desired compound as an oily product.

Reference Example 12

Preparation of 5-fluoro-1,2,3,4-tetrahydro-2-[2-(1-pyrrolidinyl)ethyl]-1-naphthalenol (1) A mixture of 5-fluoro-3,4-dihydro-1(2H)-naphthalenone (10 g), glyoxylic acid monohydrate (6.2 g)

and 85% phosphoric acid (10 ml) was stirred at 90° C. for three hours. After cooling, water was added to the reaction solution, and the precipitated crystals were collected by filtration, washed with water, and dried to give (5-fluoro-3,4-dihydro-1-oxo-2(1H)-naphthalenylidene)acetic acid (13 g).

(2) To a solution of the above acetic acid compound (20 g) and BOP Reagent (45 g) in dichloromethane (200 ml) were added with stirring pyrrolidine (10 g), and then added dropwise triethylamine (10 g) under ice-cooling, and the mixture was stirred for three hours. The mixture was washed successively with water, 10% hydrochloric acid, 10% aqueous sodium hydroxide solution and a saturated aqueous sodium chloride solution, and dried over anhydrous sodium sulfate. The resultant was concentrated under reduced pressure to remove the solvent, and the residue was purified by silica gel column chromatography (eluent; hexane:ethyl acetate=2:1) to give 5-fluoro-1,2,3,4-tetrahydro-1-oxo-2-naphthalenylidene)acetyl]pyrrolidine (15 g) as an oily product.

(3) The above amide compound (15.4 g) was suspended in ethanol (300 ml), and hydrogen gas was introduced through the mixture at 25° C. with stirring with using as a catalyst 10% palladium-carbon (1.5 g). After the theoretical amount of hydrogen gas was absorbed, the catalyst was removed by filtration. The filtrate was concentrated under reduced pressure to remove the solvent, and the residue was purified by silica gel column chromatography (eluent; hexane: ethyl acetate =2:1) to give 5-fluoro-1,2,3,4-tetrahydro-1-oxo-2-naphthalenyl)-acetyl]pyrrolidine (9.5 g) as an oily product.

$^1$H-NMR spectrum (200 MHz, CDCl$_3$, δ ppm):1.80–2.10 (m,5H),2.24–2.45(m,2H),2.80–3.03(m,2H),3.08–3.30(m,2H),3.38–3.54(m,4H), 7.15–7.34(m,2H),7.78–7.85(m,1H)

(4) The above product (9.5 g) was dissolved in tetrahydrofuran (100 ml), and thereto was added dropwise a 1M solution of borane-tetrahydrofuran complex in tetrahydrofuran (138 ml) under ice-cooling, and the mixture was stirred at 20° C. overnight. To the reaction mixture was added dropwise methanol (100 ml) under ice-cooling, and the excess amount of the reducing agent was decomposed. The mixture was concentrated under reduced pressure to remove the solvent to give the desired compound in the form of a complex with borane.

EXAMPLE 75

Preparation of tablets

| 1-[2-(5-Fluoro-3,4-dihydro-2-naphthalenyl)-ethyl]pyrrolidine hydrochloride | 15 g |
|---|---|
| Corn starch | 30 g |
| Lactose | 68 g |
| Crystalline cellulose | 30 g |
| Hydroxypropyl cellulose | 5 g |
| Light anhydrous silicic acid | 1 g |
| Magnesium stearate | 1 g |

The above components are blended and kneaded in a conventional manner, and the mixture is granulated, and compressed into 1,000 tablet cores (each 150 mg). Further, these table cores are coated by a conventional method with using hydroxypropyl methylcellulose, macrogol, titanium oxide, talc and light anhydrous silicic acid to give film-coated tablets.

EXAMPLE 76

Preparation of powder

| 1-[2-(3,4-dihydro-6,7-dimethyl-2-naphthalenyl)-ethyl]pyrrolidine hydrochloride | 20 g |
|---|---|
| D-mannitol | 935 g |
| Hydroxypropyl cellulose | 30 g |
| Magnesium stearate | 10 g |
| Light anhydrous silicic acid | 5 g |

The above components are blended, and granulated to give 2% powder preparation.

INDUSTRIAL APPLICABILITY

As explained above, 1-[ω-(3,4-dihydro-2-naphthalenyl) alkyl]cyclic amine derivatives of the formula (I), a pharmaceutically acceptable acid addition salt thereof and an N-oxide derivative thereof exhibit a potent inhibitory effect on the micturition reflex, and show low toxicity, and hence, these compounds are useful as an agent for treatment of frequent urination and urinary incontinence, or a remedy for treatment of various diseases caused by the decrease of the bladder volume capacity, which are induced by various factors.

We claim:

1. A compound of the formula (I):

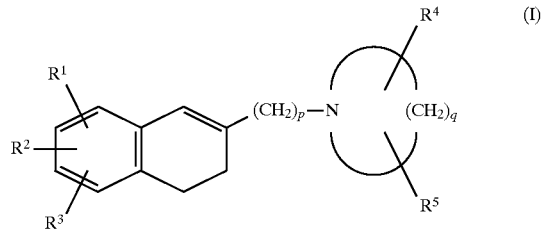

wherein $R^1$ and $R^2$ are the same or different and each a hydrogen atom, a halogen atom, a hydroxy group, a $C_1$–$C_5$ alkyl group, a $C_1$–$C_3$ alkoxy group, a hydroxymethyl group, a formyl group, a carboxyl group, or a $C_1$–$C_3$ alkoxycarbonyl group, or when $R^1$ and $R^2$ bond with carbon atoms being adjacent each other, then $R^1$ and $R^2$ may combine to form a methylenedioxy group, an ethylenoxy group (—CH$_2$CH$_2$O—), a trimethylene group, or a tetramethylene group, $R^3$ is a hydrogen atom, a halogen atom, a trifluoromethyl group, a $C_1$–$C_5$ alkyl group, a $C_1$–$C_3$ alkoxy group, or a phenyl group, $R^4$ is a hydrogen atom, a halogen atom, a hydroxy group, a $C_1$–$C_3$ alkyl group, or a ($C_1$–$C_2$ alkoxy)methyl group, $R^5$ is a hydrogen atom, a halogen atom, a $C_1$–$C_3$ alkyl group, or a ($C_1$–$C_2$ alkoxy)methyl group, or when $R^4$ and $R^5$ bond with a carbon atom other than the ones being next to the nitrogen atom, then $R^4$ and $R^5$ may combine to form an oxo group, p is an integer of from 2 to 6, and q is an integer of from 3 to 7, provided that when p is 2, and q is 5, then $R^1$, $R^2$, $R^3$, $R^4$ and $R^5$ are not simultaneously hydrogen atoms, or a pharmaceutically acceptable acid addition salt thereof, or an N-oxide derivative thereof.

2. The compound according to claim 1, wherein $R^1$ and $R^2$ are the same or different and each a hydrogen atom, a halogen atom, a hydroxy group, a methyl group, an ethyl group, a propyl group, a methoxy group, an ethoxy group, a hydroxymethyl group, a carboxyl group, a methoxycarbonyl group, or an ethoxycarbonyl group, and $R^3$ is a hydrogen atom, or a pharmaceutically acceptable acid addition salt thereof, or an N-oxide derivative thereof.

3. The compound according to claim 2, wherein $R^4$ is a hydrogen atom, a halogen atom, a hydroxy group, or a methyl group, and $R^5$ is a hydrogen atom or a methyl group, or $R^4$ and $R^5$ combine to form an oxo group, or a pharmaceutically acceptable acid addition salt thereof.

4. The compound according to claim 3, wherein $R^1$ and $R^2$ bond at 7-position and 6-position, respectively, and are the same or different and each a methyl group, an ethyl group, a methoxy group, an ethoxy group, or a hydroxymethyl group, $R^4$ and $R^5$ are the same or different and each a hydrogen atom or a methyl group, p is an integer of from 2 to 5, and q is an integer of from 3 to 7, or a pharmaceutically acceptable acid addition salt thereof.

5. The compound according to claim 4, wherein $R^4$ and $R^5$ are both hydrogen atoms, p is 2, 3 or 4, and q is 4 or 5, or a pharmaceutically acceptable acid addition salt thereof.

6. The compound according to claim 3, wherein $R^1$ is a hydrogen atom, $R^2$ is a 5-halogen atom, or $R^1$ and $R^2$ are each a halogen atom at 7-position and 6-position, respectively, $R^4$ and $R^5$ are the same or different and each a hydrogen atom or a methyl group, p is an integer of from 2 to 5, and q is an integer of from 3 to 7, or a pharmaceutically acceptable acid addition salt thereof.

7. The compound according to claim 6, wherein the halogen atom is a fluorine atom, $R^4$ and $R^5$ are both hydrogen atoms, p is 2, 3 or 4, and q is 4 or 5, or a pharmaceutically acceptable acid addition salt thereof.

8. A compound of the formula (Ia):

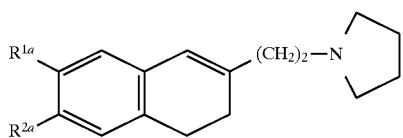

wherein $R^{1a}$ and $R^{2a}$ are the same or different, and each a methyl group, an ethyl group, a methoxy group, an ethoxy group, or a hydroxymethyl group, or a pharmaceutically acceptable acid addition salt thereof.

9. The compound according to claim 8, which is selected from 1-[2-(3,4-dihydro-6,7-dimethoxy-2-naphthalenyl) ethyl]pyrrolidine, 1-[2-(3,4-dihydro-7-methoxy-6-methyl-2-naphthalenyl)ethyl]pyrrolidine, 1-[2-(3,4-dihydro-6-hydroxymethyl-7-methyl-2-naphthalenyl)ethyl]pyrrolidine, and 1-[2-(6,7-diethyl-3,4-dihydro-2-naphthalenyl)ethyl] pyrrolidine, or a pharmaceutically acceptable acid addition salt thereof.

10. 1-[2-(3,4-Dihydro-6,7-dimethyl-2-naphthalenyl) ethyl]pyrrolidine, or a pharmaceutically acceptable acid addition salt thereof.

11. 1-[2-(5-Fluoro-3,4-dihydro-2-naphthalenyl)ethyl] pyrrolidine, or a pharmaceutically acceptable acid addition salt thereof.

12. A process for preparing a compound of the formula (I):

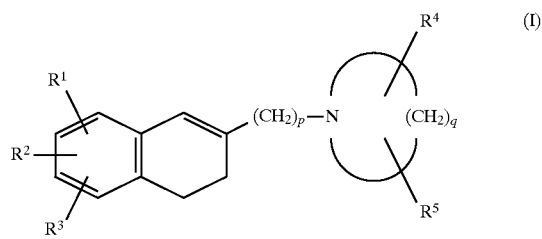

wherein $R^1$, $R^2$, $R^3$, $R^4$, $R^5$, p and q are the same as defined in claim 1, or a pharmaceutically acceptable acid addition salt thereof, or an N-oxide derivative thereof, which comprises (a) subjecting a compound of the formula (II):

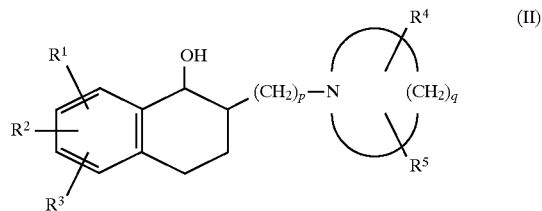

wherein $R^1$, $R^2$, $R^3$, $R^4$, $R^5$, p and q are the same as defined in claim 1, to dehydration, or (b) reacting a compound of the formula (III):

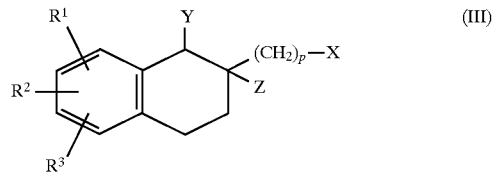

wherein $R^1$, $R^2$, $R^3$ and p are the same as defined in claim 1, X and Y are the same or different and each a reactive ester residue of an alcohol, and Z is a hydrogen atom, or Y and Z may combine to form a bond, with a compound of the formula (IV):

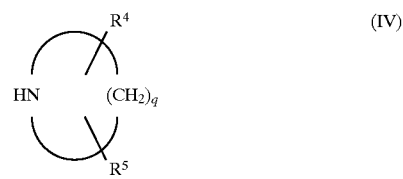

wherein $R^4$, $R^5$ and q are the same as defined in claim 1, subjecting optionally the product wherein $R^1$ and/or $R^2$ are a $C_1$–$C_3$ alkoxycarbonyl group to reduction or hydrolysis to convert it into a compound wherein $R^1$ and/or $R^2$ are a formyl group, a hydroxymethyl group, or a carboxyl group, and/or followed by converting optionally the product into a pharmaceutically acceptable acid addition salt thereof or an N-oxide derivative thereof.

13. A pharmaceutical composition comprising as an active ingredient a compound as set forth in claim 1, and a pharmaceutically acceptable carrier or diluent.

14. A pharmaceutical composition comprising as an active ingredient a compound as set forth in claim 2, and a pharmaceutical acceptable carrier or diluent.

15. A pharmaceutical composition comprising as an active ingredient a compound as set forth in claim 3, and a pharmaceutical acceptable carrier or diluent.

16. A pharmaceutical composition comprising as an active ingredient a compound as set forth in claim 4, and a pharmaceutical acceptable carrier or diluent.

17. A pharmaceutical composition comprising as an active ingredient a compound as set forth in claim 5, and a pharmaceutical acceptable carrier or diluent.

18. A pharmaceutical composition comprising as an active ingredient a compound as set forth in claim 6, and a pharmaceutical acceptable carrier or diluent.

19. A pharmaceutical composition comprising as an active ingredient a compound as set forth in claim 7, and a pharmaceutical acceptable carrier or diluent.

20. A pharmaceutical composition comprising as an active ingredient a compound as set forth in claim 8, and a pharmaceutical acceptable carrier or diluent.

21. A pharmaceutical composition comprising as an active ingredient a compound as set forth in claim 9, and a pharmaceutical acceptable carrier or diluent.

22. A pharmaceutical composition comprising as an active ingredient a compound as set forth in claim 10, and a pharmaceutical acceptable carrier or diluent.

23. A pharmaceutical composition comprising as an active ingredient a compound as set forth in claim 11, and a pharmaceutical acceptable carrier or diluent.

* * * * *

UNITED STATES PATENT AND TRADEMARK OFFICE
CERTIFICATE OF CORRECTION

PATENT NO. : 5,847,159
DATED : December 8, 1998
INVENTOR(S) : Naoki KAI et al.

It is certified that error appears in the above-identified patent and that said Letters Patent is hereby corrected as shown below:

Please note and correct:

Column 13, line 59, delete "[Japan J. Parmacol.,23, 1125 (1982)].", insert --[Japan. J. Pharmacol., 32, 1125 (1982)].--;

Column 18, line 33, delete "." after the word with.

Column 18, line 62, delete "." after the word corresponding.

Column 21, line 32, delete "eluents", insert --eluates--.

Column 24, line 28, delete "staring compounds were", insert --starting compound was--.

Column 28, line 48, delete "the" second occurrence.

Column 29, line 9, delete "were", insert --was--.
Column 29, line 64, delete "table", insert --tablet--.

Signed and Sealed this

Eighth Day of June, 1999

Attest:

Q. TODD DICKINSON

*Attesting Officer*  *Acting Commissioner of Patents and Trademarks*